United States Patent
Hudson et al.

(10) Patent No.: US 6,743,820 B2
(45) Date of Patent: Jun. 1, 2004

(54) METHODS FOR PROTECTION OF STRATIFIED SQUAMOUS EPITHELIUM AGAINST INJURY BY NOXIOUS SUBSTANCES AND NOVEL AGENTS FOR USE THEREFOR

(75) Inventors: Richard A. Hudson, Toledo, OH (US); Liyanaaratchinge M. V. Tillekeratne, Toledo, OH (US); Nelia A. Tobey, River Ridge, LA (US); Roy C. Orlando, New Orleans, LA (US)

(73) Assignee: University of Toledo, Toledo, OH (US)

( * ) Notice: Subject to any disclaimer, the term of this patent is extended or adjusted under 35 U.S.C. 154(b) by 0 days.

(21) Appl. No.: 09/900,336

(22) Filed: Jul. 5, 2001

(65) Prior Publication Data

US 2002/0052408 A1 May 2, 2002

Related U.S. Application Data

(60) Provisional application No. 60/216,771, filed on Jul. 7, 2000.

(51) Int. Cl.$^7$ .................. A61K 31/26; A61K 31/275
(52) U.S. Cl. .................. 514/516; 558/11; 558/13; 558/14; 514/520
(58) Field of Search .................. 558/11, 13, 14

(56) References Cited

U.S. PATENT DOCUMENTS

| | | |
|---|---|---|
| 3,608,061 A | 9/1971 | McNally |
| 4,328,244 A | 5/1982 | Daniel et al. |
| 4,514,416 A | 4/1985 | Fujii et al. |
| 4,570,006 A | 2/1986 | Fujii et al. |
| 4,975,281 A | 12/1990 | Harwood et al. |
| 5,011,846 A | 4/1991 | Gittos et al. |
| 5,087,638 A | 2/1992 | Belanger et al. |
| 5,141,855 A | 8/1992 | Schmittou |
| 5,189,056 A * | 2/1993 | Orlando et al. ........... 514/439 |
| 5,206,427 A | 4/1993 | Blank et al. |
| 5,360,800 A | 11/1994 | Coates et al. |
| 5,374,537 A * | 12/1994 | Orlando et al. ........... 435/29 |
| 5,495,851 A | 3/1996 | Dill et al. |
| 5,670,163 A | 9/1997 | Cuca et al. |
| 5,753,265 A | 5/1998 | Bergstrand et al. |
| 5,753,631 A | 5/1998 | Paulson et al. |
| 5,817,676 A | 10/1998 | Catlow et al. |
| 5,843,987 A | 12/1998 | Rajagopalan et al. |
| 5,858,391 A | 1/1999 | Cuca et al. |
| 5,916,910 A | 6/1999 | Lai |
| 5,955,470 A | 9/1999 | Gittos |

FOREIGN PATENT DOCUMENTS

| | | |
|---|---|---|
| EP | 0 245 855 A2 B1 | 11/1987 |
| EP | 0 732 333 A1 B1 | 9/1996 |
| EP | 0 839 530 A1 | 5/1998 |
| EP | 0 839 531 | 5/1998 |
| EP | 0 908 459 A1 | 4/1999 |
| WO | WO 94/13277 A2 A3 | 6/1994 |
| WO | WO 99/02505 A1 | 1/1999 |
| WO | WO 00/10526 A2 A3 | 3/2000 |

OTHER PUBLICATIONS

Ellison et al., "Metabolism of Orphenadrine Citrate in Man", Jour. of Pharm. and Exp. Therapeutics, vol. 176, No. 2, PP 284–295.*

Bussemakers, M.J.G. et al. (1993). "Molecular Cloning and Characterization of the Human E–Cadherin cDNA," *Molecular Biology Reports* 17:123–128.

Chung, R.S.K. et al. (Aug. 1975). "Hydrogen Ion Transport in the Rabbit Esophagus," *Am. J. of Physiol.* 229(2):496–500.

Daubresse, N. et al. (1998). "Phase Transfer Wittig Reaction with 1,3–Dioxolan–2–yl–methyltiphenyl phosphonium Salts: an Efficient Method and Vinylogation of Aromatic Aldehydes," *Tetrahedron* 54:10761–10770.

Dodd, W.J. et al. (Jul.–Aug. 1970). "Sequential Gross, Microscopic and Roentgenographic Features of Acute Feline Esophagitis," *Invest. Radiol.* 5(4):209–219.

Gennaro, A.R. ed. (1995). *Remington: Practice of the Science and Pharmacy*, Mack Publishing Co.; Pennsylvania, pp. xv–xvi (Table of Contents Only).

Harmon, J.W. et al. (Jan. 1981). "Effects of Acid and Bile Salts on the Rabbit Esophageal Mucosa," *Digestive Diseases and Sciences* 26(1):65–72.

(List continued on next page.)

*Primary Examiner*—Cecilia Tsang
*Assistant Examiner*—Ebenezer Sackey
(74) *Attorney, Agent, or Firm*—Calfee, Halter & Griswold, LLP

(57) ABSTRACT

Novel sulfate ester agents and the use of those agents for treating gastroesophageal reflux disease (GERD) are described, exemplary agents being of the formula:

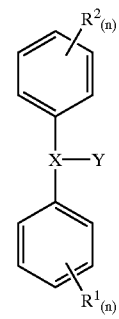

wherein X is —OCH$_2$— or —CH$_2$O—; Y is a group pendant from X comprising at least one —OSO$_3$R$^4$ moiety, wherein R$^4$ is H or a pharmaceutically acceptable cation; n is an integer from 1–3; and R$^1$ and R$^2$ are each independently selected from the group consisting of —H, a halogen with an atomic number from 9 to 53, —SO$_3$R$^4$, —NCS, —NCO, —NH(CO)—OR$^3$, —NH(CS)SR$^3$, —NH(C=NH)OR$^3$, —NHCOCH$_2$Cl, —NHCOCH$_2$Br, —NHCO—CH=CH$_2$, —NHC(O)—CF$_3$, wherein R$^4$ is H or a pharmaceutically acceptable cation.

14 Claims, 13 Drawing Sheets

OTHER PUBLICATIONS

Kidder, J.W. et al. (Oct. 1983). "Evaluation of In Vivo Measurement of Transesophageal Electrical Resistance as an Indicator of Early Experimental Esophageal Mucosal Injury," *J. Lab. Clin. Med.* 102(4):477–486.

Kivilaakso, E. et al. (Mar. 1980). "Effect of Bile Salts and Related Compounds on Isolated Esophageal Mucosa," *Surgery* 87(3):280–285.

Labeaga, L. and Orjales, A. (2000). "Pharmacological Profile of Dosmalfate," *Drugs of Today 2000* 36(Suppl. A):59–66.

Micheel, F. and Staněk J., Jr. (1972). "Bildung Carbocyclischer Verbindungen aus D–Glucose and Anisol in Wasserfreiem Fluorwasserstoff," *Liebigs Ann. Chem.* 759:37–62.

Orlando R.C. et al. (2000). "Pathophysiology of Gastroesophageal Reflux Disease: Offensive Factors and Tissue Resistance," Chapter 6 In *Gastroesophageal Reflux Disease.* Orlando, R.C. (ed.), Marcel Decker, Inc.: New York, pp. 165–192.

Orlando, R.C. and Powell, D.W. (1984). "Studies of Esophageal Epithelial Electrolyte Transport and Potential Difference in Man," In *Mechanisms of Mucosal Protection in the Upper Gastrointestinal Tract.* Allen, A. et al. (eds.), Raven Press: New York, pp. 75–79.

Orlando, R.C. (1999). "Pathophysiology of Gastroesophageal Reflux Disease: Esophageal Epithelial Resistance," Chapter 22 In *The Esophagus.* Castell, D.O. and Richter, J.E. (eds.), Lippincottt Williams & Wilkins: Philadephia, pp. 409–419.

Orlando, R.C. (Mar. 6, 2000). "Mechanisms of Reflux-Induced Epithelial Injuries in the Esophagus," *Am. J. of Med.* 108(4A):104S–108S.

Pernemalm, P. (1978). "Reaction of D–Glucose with Phenol and with Pyrogallol under Acidic Conditions," *Acta Chem. Scand.* B 32(1):72–74.

Plott, R.T. et al. (Aug. 1994). "Pemphigus Vulgaris Antigen Lacks Biochemical Properties Characteristic of Classic Cadherins," *J. of Invest. Dermatol.* 103(2):168–172.

Salo, J. and Kivilaakso, E. (Jul. 1982). "Role of Luminal $H^+$ in the Pathogenesis of Experimental Esophagitis," *Surgery* 92:61–68.

Tobey, N.A. et al. (1986). "Cytoprotective Effect of Sulfate Ions in Acid–Exposed Rabbit Esophagus." *Am. J. Physiol.* 251(Gastrointest. Liver Physiol. 14):G866–G869.

Tobey, N.A. et al. (1996). "Dilated Intercellular Spaces: A Morphological Feature of Acid Reflux—Damaged Human Esophageal Epithelium," *Gastroenterology* 111:1200–1205.

Howden, C. W. (1997). "Optimizing the Pharmacology of Acid Control in Acid–Related Disorders," *The American Journal of Gastroenterology* 92(4):17S–21S.

Hunt, R. H. (1997). "Peptic Ulcer Disease: Defining the Treatment Strategies in the Era of Helicobacter Pylori," *The American Journal of Gastroenterology* 92(4):36S–43S.

Tobey, N. A. et al. (2001). "The Role of Pepsin in Acid Injury to Esophageal Epithelium," *The American Journal of Gastroenterology* 96(11):3062–3070.

Tobey, N. A. and Orlando, R.C. (2002). "Paracellular Permeability in Healthy and Acid–Damaged Rabbit Esophageal Epithelium," *Journal of Investigative Medicine* 50:A538 (1 page total).

Tobey, N.A. and Orlando, R. C. (2002). "Regulation of Paracellular Permeability in Rabbit Esophageal Epithelium is Calcium–Dependent," *Journal of Investigative Medicine* 50:A539 (1 page total).

Tobey, N. A. and Orlando, R. C. (2002). "E–Cadherin is Important in the Regulation of Paracellular Permeability in Rabbit Esophageal Epithelium," *Journal of Investigative Medicine* 50:A650 (1 page total).

\* cited by examiner

METHODS FOR PROTECTION OF STRATIFIED SQUAMOUS EPITHELIUM AGAINST INJURY BY NOXIOUS SUBSTANCES AND NOVEL AGENTS FOR USE THEREFOR

CROSS-REFERENCE TO RELATED APPLICATIONS

This application claims priority to U.S. provisional patent application No. 60/216,771, filed Jul. 7, 2000, which is incorporated herein by reference in its entirety.

TECHNICAL FIELD

This invention relates to methods for protecting stratified squamous epithelium against injury by noxious substances. This invention also relates to novel sulfate ester agents useful in these methods. Specifically, these methods and agents may be used in the protection and treatment of tissues damaged by or susceptible to damage by noxious substances such as acid, more particularly in the treatment of gastroesophageal reflux disease (GERD) arising from acid injury.

BACKGROUND ART

Gastroesophageal reflux (GER) is the effortless movement of gastric contents from the stomach to the esophagus. It is a physiologic process, occurring in everyone, many times a day throughout life and without symptoms or signs of tissue injury. However, beginning at about 35–40 years of age, GER is increasingly associated with the symptom of heartburn and morphologic injury to the esophagus. Indeed, a Gallup poll reported that up to 44% of adult Americans experience heartburn at least monthly and up to 10% have heartburn daily. The proximate cause for the transition from GER to gastroesophageal reflux disease (GERD) is the ability of noxious materials from the stomach to contact the esophagus with sufficient duration to result in damage to the epithelium. Moreover, it is well established that the major injurious agent within the refluxate is gastric acid, though the latter may be aided by the presence of pepsin within the refluxate.

The damage resulting from acid exposure can be demonstrated morphologically and/or physiologically by changes in potential difference (PD), electrical resistance (R), or permeability to ions and molecules (Chung, R. S., et al. *Am. J. Physiol.* 229(2): 496–500, 1975; Dodds, W. J., et al. *Invest. Radiol.* 5: 209–219, 1970; Harmon, J. W., et al. *Dig. Dis. Sci.* 26: 65–72, 1981; Kidder, J. W., et al. *J. Lab. Clin. Med.* 102: 477–486, 1983; Kivilaakso, E., et al. *Surgery* 87: 280–285, 1980; Salo, J., et al. *Surgery* 92: 61–68, 1982).

The pathophysiology of acid injury has been most thoroughly explored using the rabbit esophageal epithelium as a model for the human esophageal epithelium. Both human and rabbit esophageal epithelia are $Na^+$-absorbing 'electrically-tight' stratified squamous epithelia. Each junctional complex consists of tight junctions with a few strands and an intercellular glycoprotein matrix. Moreover, rabbit and human esophageal epithelia both respond to high luminal acidity with a time-dependent biphasic change in transepithelial PD. Further, individual squamous cells utilize a basolateral membrane, acid-extruding, $Na^+/H^+$ exchanger (NHE-1 isotype) as a principal mechanism for regulation of intracellular pH (pHi) (Orlando, R. C., et al. In: Castell, D. O., et al., eds. *The Esophagus* (3 rd Edition). Philadelphia: Lippincott Williams & Wilkins, 1999, 409–419, and Orlando, R. C., et al. In: Orlando, R. C., et al., eds. *Gastroesophageal Reflux Disease*. Marcel Decker, in press).

Key observations in humans that support a similar pathogenesis for acid reflux-induced injury to human esophageal epithelium as defined in the rabbit model are: 1) luminal perfusion in vivo with high concentrations of HCl (Bernstein test) produces a similar biphasic pattern in esophageal PD (Orlando, R. C., et al. *Am. J. Med.* 108: (4A): 104S–108S, 2000, and Orlando, R. C., et al. In: Allen, A., et al., eds. *Mechanisms of Mucosal Protection in the Upper Gastrointestinal Tract*. New York: Raven Press, 1984, 75–79); and, 2) patients with both erosive and nonerosive GERD have the same morphologic hallmark of early acid damage to esophageal epithelium, i.e. dilated intercellular spaces. Tobey, N. A., et al. *Gastroenterology* 111: 1200–1205, 1996.

Previous work has shown that sodium sulfate has a cytoprotective effect in acid exposed rabbit esophagus (Tobey, N. A., et al. Am. J. Physiol. 251 (Gastrointest. Liver Physiol. 14): G866–G869, 1986). In U.S. Pat. Nos. 5,374,537 and 5,189,056 it was alleged that protection of stratified squamous epithelia against damage from noxious luminal agents, e.g. HCl, was afforded by chemical compounds having one of the following reactive groups in their molecule: $X-SO_3^-$, where X represents oxygen or carbon, and $XO_4^=$ or $X_2O_7^=$, where X represents an element from Group VIb of the periodic table or sulfur. The compounds which were shown to provide protection against injury to stratified squamous epithelia included 4-acetamido-4'-isothiocyano-2, 2'-stilbene disulfonate (SITS), 8-anilino-naphthalene-1-sulfonate (ANS), dinitrodisulfonic acid stilbene (DNDS), sulfonazo III, 4,4'-diisothiocyano-2,2'-stilbene disulfonate (DIDS), bromophenol blue, ethane disulfonate, 1,3-benzene disulfonate, sucrose octasulfate (SOS), dextran sulfate, sodium chromate, sodium dichromate, sodium molybdate, sodium tungstate and sodium sulfate. Labeaga et al. disclose dosmalfate as a gastrointestinal and esophageal cytoprotective agent (Labeaga, L. et al. Drugs of Today 2000, Vol. 36, Suppl. A: 59–66, 2000).

There is a continued need for methods and agents for treating gastroesophageal reflux disease (GERD) and other conditions associated with the exposure of stratified squamous epithelial tissue to noxious substances.

All references cited herein are hereby incorporated by reference in their entirety.

DISCLOSURE OF THE INVENTION

The present invention provides a method for protecting stratified squamous epithelium against injury by a noxious substance comprising contacting the epithelium with an effective amount of an agent comprising a) at least one aromatic group; b) at least one $-OSO_3R^4$ moiety, wherein $R^4$ is H or a pharmaceutically acceptable cation; and c) at least one $-NCS$, $-NCO$, $-NH(CO)-OR^3$, $-NH(CS)SR^3$, $-NH(C=NH)OR^3$, $-NHCOCH_2Cl$, $-NHCOCH_2Br$, $-NHCO-CH=CH_2$, or $-NHC(O)-CF_3$ moiety.

In another aspect of the invention, the present invention provides novel compounds and a method for protecting stratified squamous epithelium against injury by a noxious substance using the novel compounds comprising administering to the epithelium an effective amount of an agent comprising:

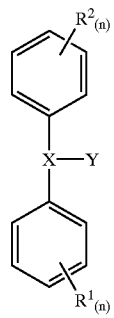

wherein: X is a linker selected from the group consisting of $C_1$–$C_6$ alkylene, $C_2$–$C_6$ alkenylene, or $C_3$–$C_6$ alkynylene, wherein X may optionally include 1 or 2 oxygen atoms and/or 1 sulfur atom; Y is a group pendant from X comprising at least one —$OSO_3R^4$ moiety, wherein $R^4$ is H or a pharmaceutically acceptable cation; n is an integer from 1–3; and $R^1$ and $R^2$ are each independently selected from the group consisting of —H, a halogen with an atomic number from 9 to 53, hydroxy, —$SO_3R^4$, —$OSO_3R^4$, —NCS, —NCO, —NH(CO)—$OR^3$, —NH(CS)$SR^3$, —NH(C=NH)$OR^3$, —$NHCOCH_2Cl$, —$NHCOCH_2Br$, —NHCO—CH=$CH_2$, —NHC(O)—$CF_3$, —S—$CH_2$—CH=$CH_2$, —$NHCH_2$—C=CH, —NH—$CH_2$—CN, —NH—S—$CH_2$—CH=$CH_2$, —O—$CH_2$—CH=$CH_2$, —NH—$CF_3$, N-mono-, di-, tri-, tetra- and penta-haloethyl, —CN, —$NH_2$, —$NO_2$, —$NHCOCH_3$, —CHO, —$COOR^4$, —$N_3$, —$COR^3$, —$R^3OH$, —$R^3NHCOCH_3$, —$R^3OSO_3R^4$, —$R^3$ $SO_3R^4$, —$OR^3$, —$SR^3$ and —$R^3$, wherein $R^3$ is p-nitrophenyl, $C_1$–$C_6$ alkyl, $C_2$–$C_6$ alkenyl, or $C_2$–$C_6$ alkynyl, if at the distal end of the substituent, or $C_1$–$C_6$ alkylene, $C_2$–$C_6$ alkenylene, or $C_2$–$C_6$ alkynylene, if at the proximal end of the substituent, and wherein $R^4$ is H or a pharmaceutically acceptable cation.

In another aspect of the invention, kits for treating an individual who suffers from or is susceptible to gastroesphageal reflux disease (GERD), heartburn, laryngitis, and pharyngitis are provided comprising a) a container comprising a dosage amount of an agent or composition as disclosed herein; and b) instructions for use.

MODES FOR CARRYING OUT THE INVENTION

Definitions

Figure 1:
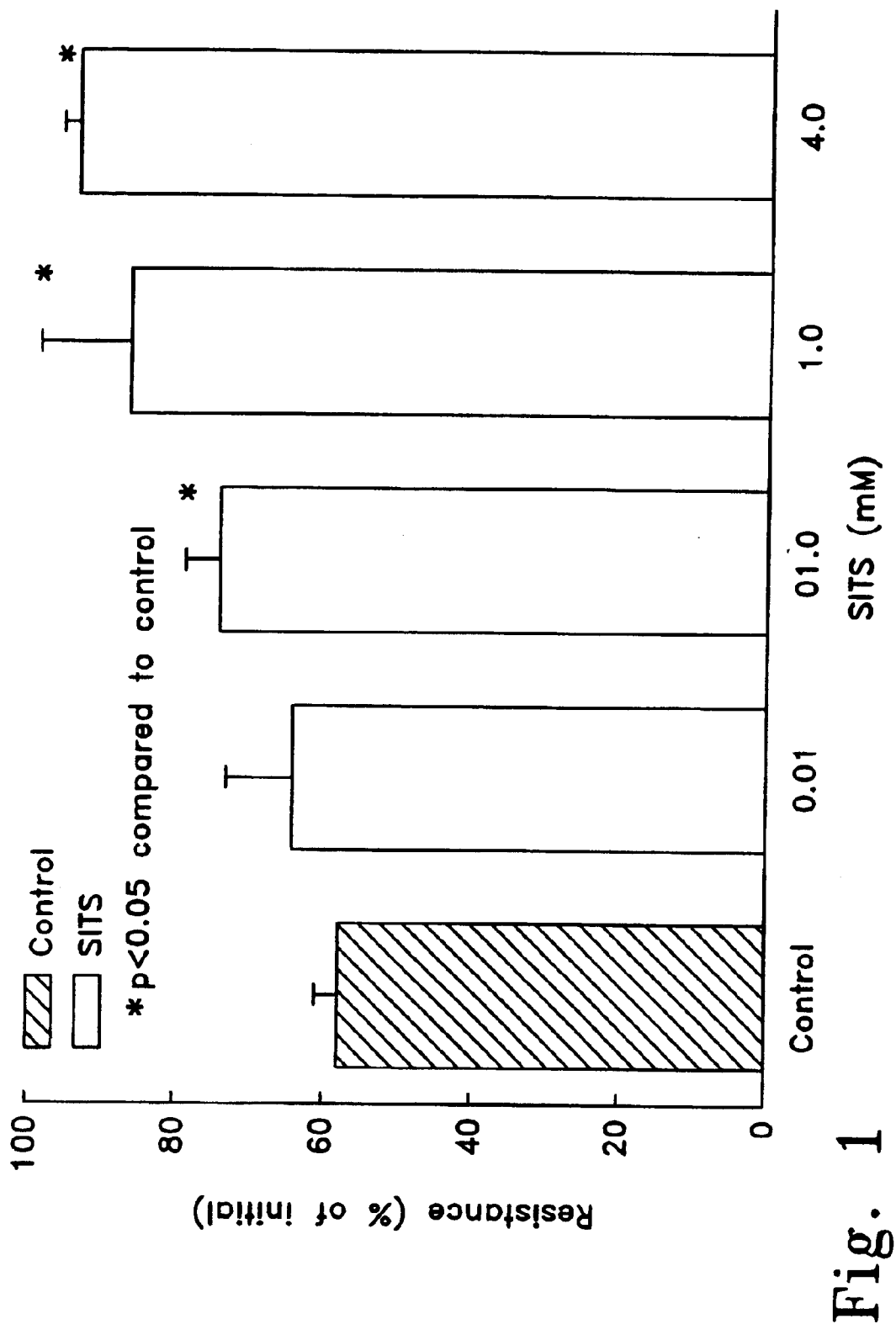
FIG. 1 is a graph showing the dose-dependent protective effect of 4-acetamido-4'-isothiocyanatostilbene-2-2'-disulfonic acid (SITS).

As used herein, the terms "agent" and "compound" may be used interchangeably, unless otherwise noted. An "agent" refers to a sulfate ester compound as described herein.

A "noxious substance", as used herein, refers to a substance which causes injury to stratified squamous epithelium in vivo. Examples of such "noxious substances" include acids or other substances, including, but not limited to, gastric acid, HCl, N-acetylcysteine, pepsin, acid-pepsin, or other irritant which contacts epithelial tissue.

An "individual" is a vertebrate, preferably a mammal, more preferably a human. Mammals include, but are not limited to, farm animals (e.g. pigs, sheep, horses and cows), sport animals, primates, rodents and pets.

A "susceptible individual" is an individual who suffers from, is suffering from, or is likely to or predisposed to suffer from a condition(s) which causes contact or exposure between their epithelial tissue(s) and a noxious substance(s). In humans these conditions may include, for example, gastroesophageal reflux disease (GERD), heartburn, indigestion, laryngitis, Barrett's Esophagus, or pharyngitis. In animals these conditions may include, for example, peptic ulcer of the forestomach.

"A", "an" and "the" include plural references unless the context clearly dictates otherwise.

"An effective amount" of an agent is an amount which reduces damage from noxious substances on stratified squamous epithelium in vivo, or reduces the symptoms of conditions or diseases associated with damage by noxious substances on stratified squamous epithelium.

The terms "injury" or "damage" as used herein are interchangeable and refer to the cellular and morphological manifestations and symptoms resulting from exposure to or contact with a noxious substance. Injury may be indicated in the individual in vivo, and may also be indicated in vitro using, for example, biopsy samples from the individual. Indications of injury or damage include, but are not limited to, acid-induced decline in potential difference (PD), prominently dilated intercellular spaces, increased permeability of intercellular junctions to noxious substances; macroscopic erosions and ulceration of epithelial tissue, cell edema, inflammation and necrosis, peptic stricture, Barrett's Esophagus, heartburn, laryngitis, pharyngitis, hoarseness and sore throat.

The terms "stratified squamous epithelium", "stratified epithelium", and "epithelium" are interchangeable as used herein. Sources of stratified squamous epithelium include, for example, buccal, oropharyngeal, esophageal and laryngeal epithelium, rumen and forestomach.

The term "protection" as used herein refers to the reduction of damage by a noxious substance to epithelium which has been contacted with an agent in vivo. The protection provided by the agent may last for at least 1 hour, at least 2 hours, at least 4 hours, at least 8 hours, at least 12 hours, at least 24 hours after contact with the agent.

The terms "activity" and "biological activity" used herein are interchangeable, and refer to the ability of a particular agent or compound to protect epithelial tissue against injury or damage from noxious substances.

Chemical terms, unless otherwise defined, are used as known in the art.

Sulfate Ester Compounds

The sulfate ester agents which are used in a first aspect of the invention are characterized by comprising at least one aromatic group, at least one —$OSO_3R^4$ moiety, where $R^4$ is H or a pharmaceutically acceptable cation such as Na or K, and at least one —NCS, —NCO, —NH(CO)—$OR^3$, —NH(CS)$SR^3$, —NH(C=NH)$OR^3$, —$NHCOCH_2Cl$, —$NHCOCH_2Br$, —NHCO—CH=$CH_2$, or —NHC(O)—$CF_3$ moiety.

Preferably, the at least one aromatic group(s) is selected from the group consisting of phenyl, pyridyl, naphthyl, quinolyl and isoquinolyl. More preferably, the at least one aromatic group(s) is phenyl. In one embodiment, the agent comprises at least two aromatic groups. In another embodiment, the agent further comprises a $C_3-C_8$ cycloalkyl. In a preferred embodiment, the at least one —$OSO_3R^4$ moiety is non-annular to the aromatic group. In another preferred embodiment, the agent comprises at least one —NCS moiety.

Another aspect of the present invention includes agents which protect stratified squamous epithelium against injury by a noxious substance, and are of the formula:

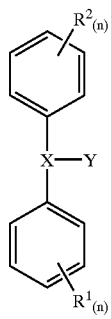

wherein: X is a linker selected from the group consisting of $C_1-C_6$ alkylene, $C_2-C_6$ alkenylene, or $C_3-C_6$ alkynylene, wherein X may optionally include 1 or 2 oxygen atoms and/or 1 sulfur atom; Y is a group pendant from X comprising at least one —$OSO_3R^4$ moiety, wherein $R^4$ is H or a pharmaceutically acceptable cation such as Na or K; n is an integer from 1–3; and $R^1$ and $R^2$ are each independently selected from the group consisting of —H, a halogen with an atomic number from 9 to 53 (i.e., F, Cl, Br, I), hydroxy, —$SO_3R^4$, —$OSO_3R^4$, —NCS, —NCO, —NH(CO)—$OR^3$, —NH(CS)$SR^3$, —NH(C=NH)$OR^3$, —$NHCOCH_2Cl$, —$NHCOCH_2Br$, —NHCO—CH=$CH_2$, —NHC(O)—$CF_3$, —S—$CH_2$—CH=$CH_2$, —$NHCH_2$—C=CH, —NH—$CH_2$—CN, —NH—S—$CH_2$—CH=$CH_2$, —O—$CH_2$—CH=$CH_2$, —NH—$CF_3$, N-mono-, di-, tri-, tetra- and penta-haloethyl, —CN, —$NH_2$, —$NO_2$, —$NHCOCH_3$, —CHO, —$COOR^4$, —$N_3$, —$COR^3$, —$R^3OH$, —$R^3NHCOCH_3$, —$R^3OSO_3R^4$, —$R^3SO_3R^4$, —$OR^3$, —$SR^3$ and —$R^3$, wherein $R^3$ is p-nitrophenyl, $C_1-C_6$ alkyl, $C_2-C_6$ alkenyl, or $C_2-C_6$ alkynyl, if at the distal end of the substituent, or $C_1-C_6$ alkylene, $C_2-C_6$ alkenylene, or $C_2-C_6$ alkynylene, if at the proximal end of the substituent, and wherein $R^4$ is H or a pharmaceutically acceptable cation such as Na or K.

Preferably, X is selected from the group consisting of —$CH_2CH_2$—, —$OCH_2$—, —$CH_2O$—, —$OCH_2CH_2$—, —$CH_2CH_2O$—, —SO—$CH_2$—, —$CH_2$—SO—, —OSO—$CH_2$—, —$CH_2$—OSO—, —CH=CH—, —$SCH_2$—, —$CH_2S$— and —$CH_2$—. Still more preferably, X is —$OCH_2$— or —$CH_2O$—.

The pendant group Y may be, for example, $C_1-C_{10}$ alkyl, $C_2-C_{10}$ alkenyl, or $C_2-C_{10}$ alkynyl, more preferably $C_1-C_6$ alkyl, $C_2-C_6$ alkenyl, or $C_3-C_6$ alkynyl, still more preferably $C_1-C_4$ alkyl, to which is attached at least one —$OSO_3R^4$ moiety, wherein $R^4$ is H or a pharmaceutically acceptable cation. Y may be straight, branched, aromatic or cyclic-aliphatic, and may also optionally include at least one hydroxyl group. In one embodiment, Y comprises a sulfonated polycarbinol chain of 1 to 6 sulfonated carbon atoms. In one embodiment, Y comprises 2 to 6 —$OSO_3R^4$ moieties. In a preferred embodiment, Y comprises at least two —$OSO_3R^4$ moieties. In another preferred embodiment, Y is a branched $C_1-C_6$ alkyl group. In an especially preferred embodiment, Y comprises ethyl-1,2-disulfate.

Preferably at least one of $R^1$ or $R^2$ is —NCS, and more preferably at least one $R^1$ and at least one $R^2$ are —NCS. In one embodiment, the at least one $R^1$ and $R^2$ groups are ortho or para-substituents. In a preferred embodiment, the at least one $R^1$ and $R^2$ groups are para-substituents.

Preferred compounds of the above formula are:

CDDD-1185

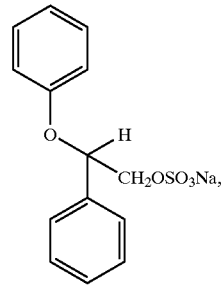

CDDD-1187

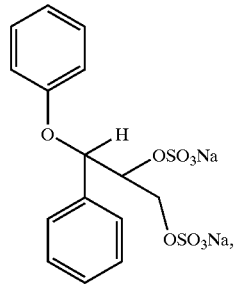

CDDD-1188

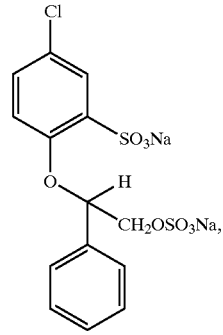

-continued

CDDD-1189

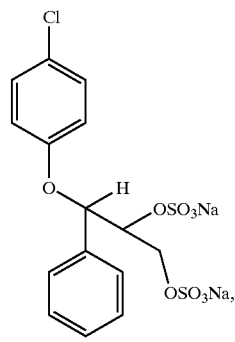

CDDD-1190

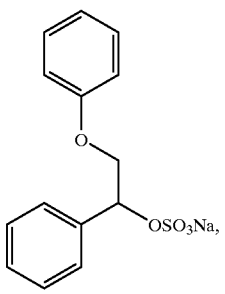

CDDD-1192

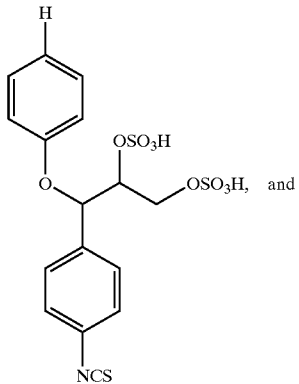

CDDD-1193

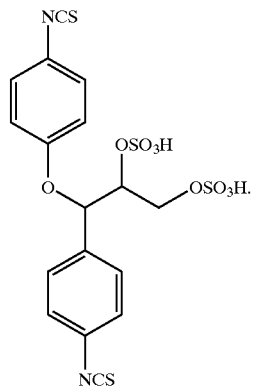

Particularly preferred compounds are

CDDD-1192

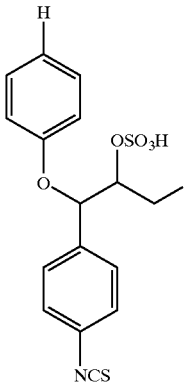     and

CDDD-1193

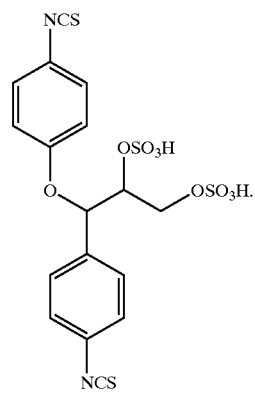

Examples of other compounds of the above formula are 1,1-bis(3-amino-4-methylphenyl)hexane-2,3,4,5,6-pentasulfate, pentasodium salt; 5-(4-azido-2-bromophenyl)-5-[4-(prop-2-enylthioamino)benzylsulfonyl]-pent-2-ene-1,4-disulfate, disodium salt; 1-(4-chloro-2,6-disulfophenyl)-4-hydroxy-4-[2-[4-(methylthiothiocarbonylamino)phenylethylene]-hex-2-yne-6-sulfate, trisodium salt; 5-[4-(cyanomethylamino)phenyl]-2-(4-formyl-2-sulfophenyl)-1-phenylpentane-1-sulfate, disodium salt; 1-(4-isothiocyanato-2-methylphenyl)-3-methylsulfate-1-(4-prop-2-enylthiophenylthio)-butane-2,4-disulfate, trisodium salt; 2-(4-chlorophenyl)-1-(cyclohexane-2,4,6-trisulfate)-1-hydroxy-2-[2-(4-nitrophenyl)ethoxy]ethane, trisodium salt; 1-(4-carbomethoxyaminophenyl)-4-phenyl-hepta-2,4-diene-6,7-disulfate, disodium salt; 5-(4-isocyalatophenyl)-5-[(4-trifluoroacetamidophenyl)thionyl]pent-2-yne-1,4-disulfate, disodium salt; 4-(4-bromoacetamido)-6-(4-isocyanatophenyl)-hexane-1,2-disulfate, disodium salt; 1-[3-(2,2-dichloroethyl)phenyl]-3-(4-prop-2-ynylaminophenyl)pent-1-yne-3-ene-5-sulfate, sodium salt; and 1-(4-trifluoromethylaminophenyl)-2-(4-isothiocyanatophenyl)-non-1-ene-3,8-disulfate, disodium salt.

General Synthetic Methods

The following illustrates a synthesis scheme for making certain embodiments of the invention and starting materials therefor.

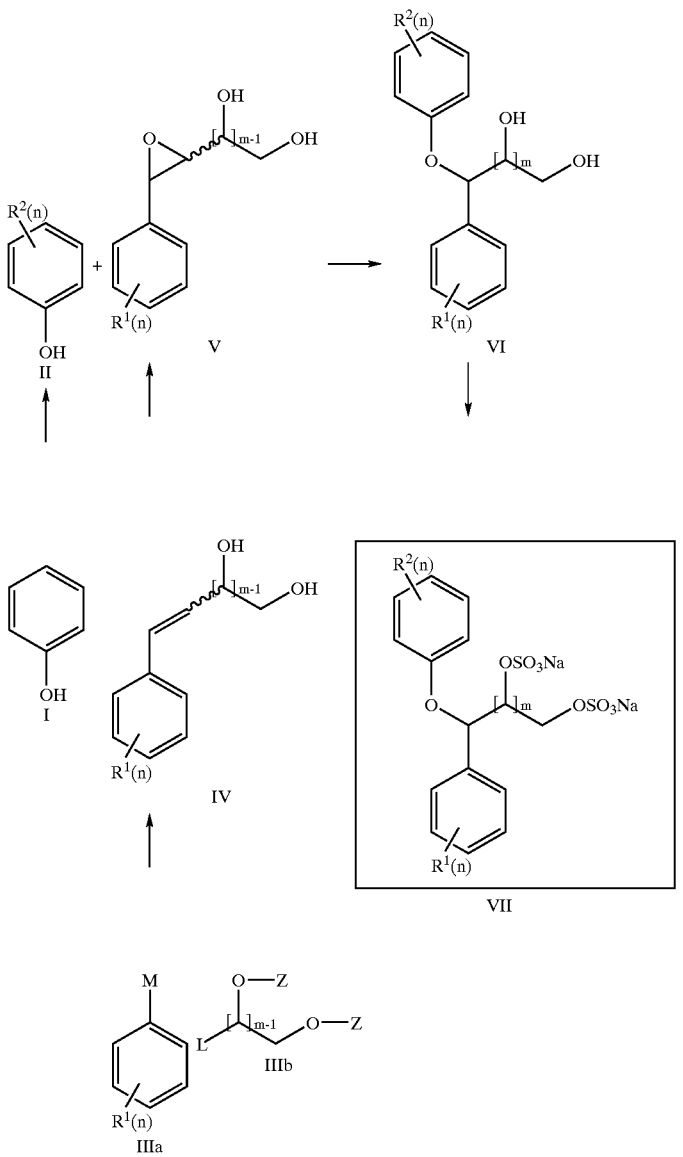

M and L are suitable moeties for forming olefins (e.g., —CHO and —CH$_2$Br for a Wittig reaction), Z is a suitable hydroxyl protecting group, and m is 0–9. The synthesis of compounds of the general type indicated in structure VII is shown above. In general, many phenolic derivatives (II) may be obtained through sequential electrophilic substitution of phenols or by direct substitution of commercially available mono-substituted phenols or by other published methods. Substituted carbinol styrene epoxides with the general structure V may be obtained from the epoxidation of the corresponding olefins (IV), which are in turn obtained from olefin-forming reactions from the fragments IIIa and IIIb.

In general, reaction of the substituted phenol (II) with the appropriate substituted carbinol sytrene epoxide (V) leads to epoxide ring opening, preferentially at the benzyl carbon to give phenoxypropane diols with the general structure VI. These products may then be sulfonated to yield the polysulfated products (VII) and further modified (if required) by reactions that convert R$^1$ or R$^2$ into other substituents.

This general scheme was used in the synthesis of compounds CDDD-1187, 1189, 1192 and 1193, which are described below in greater detail in Examples 2, 4 and 6. A variety of other compounds may be synthesized by substituting fragment IIIb with other fragments (e.g., C$_1$–C$_{10}$ a carbon skeleton which may contain suitably protected hydroxyl groups), or such as described in the synthesis of compounds CDDD-1185, 1188 and 1190 (Examples 1, 3 and 5). Selection of a suitable hydroxyl protecting group Z for compound V can enable further modification of the hydroxyl group formed after epoxide ring opening to form VI.

Other compounds with different linker groups may be formed, for example, by substitution of compounds I and IIIa. For example, substitution of phenol (I) with thiophenol yields compounds with the linker —SCH$_2$—, which may be oxidized to —SOCH$_2$— or —OSOCH$_2$—. Additional carbon atoms can be included in the linker, for example, by substituting phenol (I) with, e.g., C$_6$H$_5$—(CH$_2$)$_x$—OH, where x is 1–8, or by substituting M in compound IIIa with longer chain aldehydes, e.g., —(CH$_2$)$_x$CHO.

Alkenylene linkers may be formed by the following general reaction:

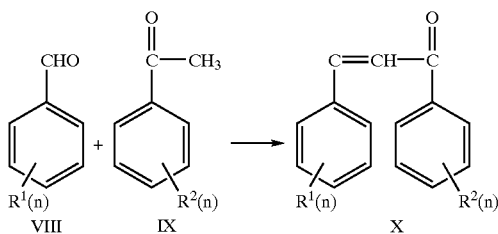

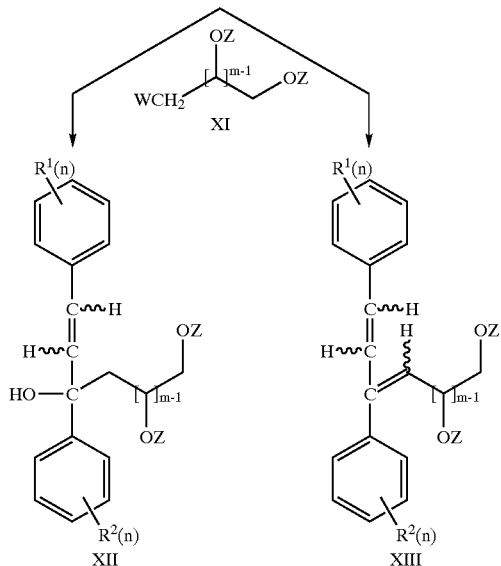

where m and Z are as above. Compounds of the formula XII may be made through an organometallic addition reaction with the fragment XI (W is e.g., —Li, —MgBr, or —MgCl), and compounds of the formula XIII may be made from a Wittig reaction with the fragment XI (W is e.g., —Br). The fragment XI may also comprise other $C_1$–$C_{10}$ carbon backbones which contain one or more protected hydroxyl groups. Analogous alkynylene linker compounds may be made as above by conversion of compound X into the analogous alkyne. Additional carbon atoms can be included in the linker, for example, by using compounds with 1 to 7 additional —($CH_2$)— groups between the phenyl and formyl in VIII, and between the phenyl and acetyl in IX.

Compounds of type XVII may be made by reaction of suitably hydroxyl-protected monosaccharide (or other $C_1$–$C_{10}$ carbon backbone which contains one or more protected hydroxyl groups) acid chlorides XIV in sequential reaction with organo-magnesium or cadmium compounds (XV and XVI) derived from Grignards, according to the following general scheme:

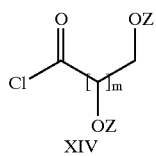

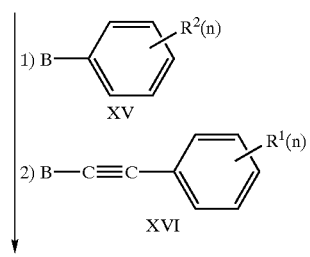

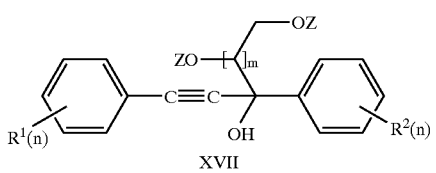

where m and Z are as above, and B is, e.g., —MgBr or —CdBr. Analogous alkenylene linkers may be made by substitution of XVI with the analogous alkene.

Linkers of the type —CH═CH— may be synthesized by the following general reaction:

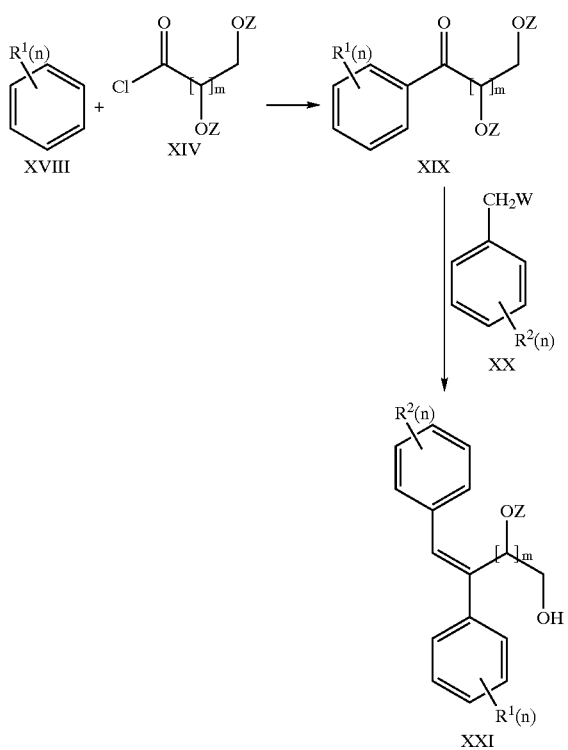

where m and Z are as above, and W is a group suitable for a Wittig reaction (e.g., —Br). Substituted benzenes XVIII are electrophilically substituted with a suitably hydroxyl-protected monosaccharide (or other $C_1$–$C_{10}$ carbon backbone which contains one or more protected hydroxyl groups) acid chloride XIV to form compounds of the type XIX. A Wittig reaction with substituted benzyl compound XX typically yields both cis and trans isomers of XXI, which can be separated through subsequent purification.

Alkylene linkers can be prepared by reduction (hydrogenation) of the corresponding alkene or alkyne bonds present in the linker groups of the above structures and schemes. Methods of forming a —$CH_2$— linker may be found in, for example, Pememalm, P. *Acta. Chem. Scand.*, B32 No.1: pp.72–74 (1978) and Micheel, F., et al. *Liebigs. Ann. Chem.*, 759: pp.37–62 (1972).

Formulation and Administration

The agents used in the invention will typically be formulated with a pharmaceutically acceptable excipient(s). Pharmaceutical excipients are well known in the art and need not be described in detail herein. A pharmaceutically acceptable excipient is a relatively inert substance that facilitates administration of a pharmacologically effective substance. Suitable excipients include but are not limited to diluents, fillers, stabilizing agents, buffers, wetting and emulsifying agents, salts for varying osmolarity and encapsulating agents. Examples of pharmaceutically acceptable excipients are described in *Remington's Pharmaceutical Sciences* (Alfonso R. Gennaro, ed., 19th edition, 1995).

The compositions comprising the agents disclosed herein may also be formulated to include or administered in conjunction with other agents for treating the gastrointestinal tract, such as histamine $H_2$ receptor blockers, gastric proton pump inhibitors, motility agents (gastroprokinetics), antacids and/or antiulcerative agents. Nonlimiting examples of these additional agents include those selected from the group consisting of cinitapride, cisapride, fedotozine, loxiglumide, alexitol sodium, almagate, aluminum hydroxide, aluminum magnesium silicate, aluminum phosphate, azulene, basic aluminum carbonate gel, bismuth aluminate, bismuth phosphate, bismuth subgallate, bismuth subnitrate, calcium carbonate, dihydroxyaluminum aminoacetate, dihydroxyaluminum sodium carbonate, ebimar, magaldrate, magnesium carbonate hydroxide, magnesium hydroxide, magnesium oxide, magnesium peroxide, magnesium phosphate (tribasic), magnesium silicates, potassium citrate, sodium bicarbonate, aceglutamide aluminum complex, acetoxolone, aldioxa, arbaprostil, benexate hydrochloride, carbenoxolone, cetraxate, cimetidine, colloidal bismuth subcitrate, ebrotidine, ecabet, enprostil, esaprazole, famotidine, gefamate, guaiazulene, irsogladine, lansoprazole, misoprostol, nizatidine, omeprazole, esomeprazole, omoprostil, γ-Oryzanol, pantoprazole, pifamine, pirenzepine, plaunotol, polaprezinc, rabeprazole, ranitidine, rebamipide, rioprostil, rosaprostol, rotraxate, roxatidine acetate, sofalcone, spizofarone, sucralfate, telenzepine, teprenone, trimoprostil, trithiozine, troxipide and zolimidine.

The dosages of these additional agents for treating the gastrointestinal tract may vary depending upon the severity of the condition and the particular biochemistry and need of the patient. The dosages of the active ingredients may also vary depending upon whether the active ingredients are administered in tablet or liquid form or other suitable delivery method. A physician or clinician may readily determine suitable dosages. Examples of suitable agents for treating the gastrointestinal tract may be found in *The Merck Index* (Budavari, S., et al., eds., 12th Edition, 1996) and in the *Physicians' Desk Reference* (52nd edition, 1998).

Other therapeutic compounds which may be included in the formulation of or administered in conjunction with the compositions of the invention include agonists, partial agonists and antagonists of the 5-$HT_3$ and 5-$HT_4$ receptors, such as Lotronex® (alosetron HCl) and Zelmac® (tegaserod), which are described in U.S. Pat. No. 5,360,800 and PCT Publication No. WO 00/10526, respectively.

Preferred formulations include those which slowly release the agent over time, such as found in lozenges, gums, and buccal patches. Another preferred formulation includes formulating the agent in a bioadherent ingestible composition, such as those found in U.S. Pat. Nos. 5,858,391 and 5,670,163 to Cuca, et al. The agent may also be formulated as a liquid or as a tablet, pill, capsule or powder to be dissolved in a liquid, and is preferably slowly sipped by the patient.

The protective agents disclosed herein and compositions comprising the agents may be administered by perfusion via a tube on to the surface of stratified squamous epithelia, by oral ingestion, gum or lozenge (for treatment of oropharyngeal, rumen, forestomach and esophageal epithelium), by mouth rinse (for oropharyngeal, tongue and buccal epithelium), by aerosol spray (for oropharyngeal, buccal, tongue, laryngeal or vocal cord epithelium), or by other means.

Particular embodiments encompass where the agent provides protection against damage by a noxious substance to the epithelium after a short period of contact with the epithelium. In certain embodiments the period of contact can be, for example, less than or equal to 1 hour, less than or equal to 30 minutes, less than or equal to 15 minutes, less than or equal to 10 minutes, less than or equal to 5 minutes, less than or equal to 1 minute. In a preferred embodiment the epithelium is contacted with or exposed to the agent for about 1 to 5 minutes.

Dosing and Regimen

The agent may be administered at a dosage of, for example, about 0.01–250 mg/day, about 0.1–250 mg/day, about 0.1–50 mg/day, about 0.1–10 mg/day. In preferred embodiments, the concentration of the agent administered is about 4 nM–4 mM, about 40 nM–40 $\mu$M, about 40nM–4$\mu$M, about 4 $\mu$M–40 $\mu$M. In preferred embodiments, the concentration of the agent is less than 1 mM, preferably less than 0.1 mM, even more preferably less than 0.01 mM, even more preferably sub micromolar.

The agent may be administered at least 1×, 2×, 5×, 10× or 20×. A preferred embodiment includes where the agent is administered at least once a day for a period of days, weeks, months or years. The agent may be administered at least once, twice or three times daily.

When formulated as a liquid, or as a tablet, pill, capsule or powder to be dissolved in a liquid, the formulation comprising the agent is preferably slowly sipped by the individual.

The present invention also includes a method for treating gastroesophageal reflux disease (GERD), comprising administering a cytoprotective agent to an individual suffering from GERD at a first dosage amount and/or dosing schedule for a period of time (e.g. until the individual's symptoms improve), followed by administering the cytoprotective agent to the individual at a second lower dosage amount and/or less frequent dosing schedule for a period of time (e.g., as the individual's symptoms improve), and optionally followed by further reducing the dosage amount and/or dosage frequency as the individual's symptoms continue to improve. For instance, the agent may initially be administered, e.g., four times per day, until the individual's symptoms improve, at which point the dosage frequency may be gradually reduced to, e.g., three times per day, two times per day, once per day. Alternatively, the agent may be administered initially at a higher dosage, and gradually reduced to a lower dosage as the individual's symptoms continue to improve.

An additional embodiment includes where the agent is administered from between 0 minutes to 24 hours prior to exposure to a noxious substance. Additional embodiments include where administration of the agent is at least 1 minute, at least 30 minutes, at least 60 minutes, at least 2 hours, at least 4 hours, at least 8 hours, at least 12 hours, at least 24 hours prior to contact or exposure to a noxious substance.

An additional embodiment includes where the agent is administered from between 0 minutes to 24 hours prior to food consumption by the individual. Additional embodiments include where administration of the agent is at least 1 minute, at least 30 minutes, at least 60 minutes, at least 2 hours, at least 4 hours, at least 8 hours, at least 12 hours, at least 24 hours prior to food consumption by the individual.

In a preferred embodiment, an agent, such as CDDD-1193 or CDDD-1192 is administered orally to a subject with symptoms (e.g. heartburn, acid regurgitation, acid indigestion) and/or signs of GERD (e.g. erosions). An adult of average size would be expected to ingest an aqueous solution containing, for example, 4 nM–4 mM of a selected agent from one to four times a day (total dose in milligrams would depend on the molecular weight, potency and dosing regimen of the selected agent). In one embodiment, a tablet comprising the agent would be dissolved in a glass of water to produce an approximately 40 nM–4$\mu$M solution of the agent (or the agent would be provided in an aqueous solution comprising the agent at a concentration of about 40 nM–4$\mu$M), and the solution would be sipped slowly by the individual over 5–10 minutes once a day.

Kits for the Administration of Sulfate Ester Agents

Also provided by the present invention are kits comprising the agent(s) and compositions as described herein for the administration of the agents and compositions to susceptible individuals. Kits may comprise a dosage amount of an agent or composition comprising the agent as disclosed herein. Kits may further comprise suitable packaging and/or instructions for use of the agent.

The invention is further illustrated by the following nonlimiting examples. The reported tests for the previously disclosed compounds SITS and SOS are presented for comparison purposes.

EXAMPLES

NMR spectra were obtained on a Bruker AC-F 300 spectrometer in the solvent specified in each case. Chemical shifts are in ppm relative to the solvent peak or TMS. All of NMR spectra are consistent with the structures assigned.

Example 1

Synthesis of 2-Phenoxy-2-phenylethanesulfate, sodium salt (CDDD 1185)

A mixture of phenol (28.2 g), NaOH (4.0 g) and water (15 ml) was heated on a boiling water bath until the mixture became homogeneous. Styrene oxide (12.0 g) was added dropwise over a period of 15 minutes and the mixture was heated with stirring on a boiling water bath for 1 hr. The mixture was poured into a solution of NaOH (12.0 g) in ice water (200 ml) and extracted with ether (50 ml) 2 times. The ether solution was dried over anhydrous sodium sulfate and the solvent distilled off to obtain a crystalline product. Recrystallization from methylene chloride-hexane gave white crystals (6.6 g) of 2-phenoxy-2-phenylethanol.

2-Phenoxy-2-phenylethanol (4.28 g) prepared as described above was dissolved in dry pyridine (20 ml) and was treated with pyridine-sulfur trioxide (7.16 g). The mixture was heated with stirring at 60° C. for 4 hrs. Pyridine was distilled off under reduced pressure and the residue was dissolved in water and neutralized with NaOH solution. The aqueous solution was extracted with ether and was evaporated to dryness. The residue was crystallized from water to obtain white crystals (3.1 g) of 2-phenoxy-2-phenylethanesulfate, sodium salt (CDDD 1185), $^1$H NMR ($D_2O$) $\delta$4.18 (m, 2H), 5.46 (m, 1H), 6.80 (m, 3H), 7.06 (t, 2H), 7.19 (m, 3H), 7.28 (m, 2H); $^{13}$C NMR ($D_2O$) $\delta$72.00 ($CH_2$), 79.18 (CH), 117.43 (CH), 122.83 (CH), 127.81 (CH), 129.61 (CH), 129.77 (CH), 130.63 (CH), 137.51 (C), 157.80 (C).

Example 2

Synthesis of (2R, 3S)-3-Phenoxy-3-phenylpropane-1,2-disulfate, disodium salt (CDDD 1187)

A mixture of phenol (9.4 g), NaOH (1.33 g) and water (6.6 ml) was heated on a boiling water bath until the mixture became homogeneous. (2R, 3R)-3-Phenylglycidol (5.0 g) was added in small portions over a period of 10 minutes and the mixture was heated with stirring on a boiling water bath for 1 hr. The mixture was poured into a solution of NaOH (3.99 g) in ice water (75 ml) and extracted with ether (50 ml) 2 times. The ether solution was dried over anhydrous sodium sulfate and the solvent distilled off to obtain a white solid. Recrystallization from methylene chloride gave white crystals (3.1 g) of (2R, 3S)-3-phenoxy-3-phenylpropane-1,2-diol.

(2R, 3S)-3-Phenoxy-3-phenylpropane-1,2-diol (6.1 g) prepared as described above was dissolved in dry pyridine (35 ml) and was treated with pyridine-sulfur trioxide (11.9 g). The mixture was heated with stirring at 60° C. for 4 hrs. Pyridine was distilled off under reduced pressure and the residue dissolved in water and neutralized with NaOH solution. The aqueous solution was extracted with ether and evaporated to dryness. Most of the inorganic impurities were removed by crystallization from water-MeOH and the filtrate was evaporated to dryness. After an unsuccessful attempt to extract the product with acetonitrile in a Soxhlet, the residue was crystallized from water-MeOH to obtain white crystals of (2R, 3S)-3-phenoxy-3-phenylpropane-1,2-disulfate, disodium salt (CDDD 1187), mp 156–158° C., $^1$H NMR ($D_2O$) δ4.21 (dd, 1H, J=10.99, 3.55 Hz), 4.34 (dd, 1H, J=10.99, 4.86 Hz), 4.76 (m, 1H), 5.54 (d,1H, J=5.25), 6.84 (m, 3H), 7.12 (t, 2H, J=8.1 Hz), 7.25 (m, 2H), 7.36 (d, 2H, J=6.73 Hz), $^{13}$C NMR ($D_2O$) δ66.55 ($CH_2$), 79.08 (CH), 80.21 (CH), 117.24 (CH), 122.69 (CH), 128.25 (CH), 129.39 (CH), 129.52 (CH), 130.54 (CH), 137.12 (C), 157.89 (C).

Example 3
Synthesis of 2-(4-Chloro-2-sulfophenoxy)-2-phenylethanesulfate, disodium salt (CDDD 1188)

A mixture of 5-chloro-2-hydroxybenzenesulfonic acid, sodium salt (7.9 g), NaOH (1.37 g) and water (25 ml) was heated on a boiling water bath until the mixture became homogeneous. Styreneoxide (2.4 g) was added dropwise over a period of 10 minutes and the mixture was heated with stirring on a boiling water bath for 1 hr. It was extracted with ether and the aqueous solution was evaporated to dryness. The residue was treated with water and the insoluble white precipitate was collected by filtration and washed with 5 mL water to obtain 2-(4-chloro-2-sulfophenoxy)-2-phenylethanol (4.1 g).

2-(4-chloro-2-sulfophenoxy)-2-phenylethanol (6.0 g) prepared as described above was dissolved in dry pyridine (12 ml) and was treated with pyridine-sulfur trioxide (4.08 g). The mixture was heated with stirring at 60° C. for 4 hrs. Pyridine was distilled off under reduced pressure and the residue was dissolved in water. The resulting solution was made slightly alkaline with 10% NaOH solution and extracted with ether. The aqueous solution was evaporated to dryness. The inorganic impurities were removed by precipitation from water-MeOH. The filtrate was evaporated to dryness and recrystallized from water-MeOH to obtain white crystals (5.1 g) of 2-(4-chloro-2-sulfophenoxy)-2-phenylethanesulfate, disodium salt (CDDD 1188), 164–165° C. (decomp.), $^1$H NMR ($D_2O$) δ4.19 (dd, 1H, J=10.99, 4.38 H z) 4.38 (dd, 1HJ=10.9, 7.27 Hz), 5.67 (m, 1H), 6.83 (d, 1H, J=8.9 Hz), 7.15 (dd, 1H, J=8.9, 2.64 Hz), 7.26 (m, 3H), 7.43 (d, 2H, J=6.68 Hz), 7.64 (d, 1H, J=1.49 Hz), $^{13}$C NMR ($D_2O$) δ71.92 ($CH_2$), 79.14 (CH), 117.36 (CH), 125.72 (C), 128.06 (CH), 129.17 (CH), 129.76 (CH), 133.11 (CH), 133.38 (C), 137.24 (C), 153.63 (C).

Example 4
Synthesis of (2R, 3S)-3-(4-Chlorophenoxy)-3-phenylpropane-1,2-disulfate, disodium salt (CDDD 1189)

A mixture of 4-chlorophenol (15.42 g), NaOH (1.6 g) and water (8 ml) was heated on a boiling water bath. (2R, 3R)-3-Phenylgycidol (6.0 g) was added in small portions over a period of 10 minutes and the mixture was heated with stirring on a boiling water bath for 1 hr. The reaction mixture was cooled and treated with a solution of NaOH (4.8 g) in water (80 ml). The resulting solution was extracted with ether. The ether solution was dried over anhydrous sodium sulfate and the solvent was distilled off to obtain a colorless oil (8.8 g) of (2R, 3S)-3-(4-chlorophenoxy)-3-phenylpropane-1,2-diol.

(2R, 3S)-3-(4-chlorophenoxy)-3-phenylpropane-1,2-diol (8.0 g) prepared as described above was dissolved in dry pyridine (30 ml) and treated with pyridine-sulfur trioxide (13.7 g). The mixture was heated with stirring at 60° C. for 4 hrs. Pyridine was distilled off under reduced pressure and the residue dissolved in water and made slightly alkaline with 10% NaOH solution. The aqueous solution was extracted with ether and was evaporated to dryness. Most of the inorganic impurities were removed by crystallization from water-MeOH and the filtrate was evaporated to dryness. The residue was crystallized from acetonitrile-ether to obtain white crystals (4.8 g) of (2R, 3S)-3-(4-chlorophenoxy)-3-phenylpropane-1,2-disulfate, disodium salt (CDDD 1189), mp 184–185° C., $^1$H NMR ($D_2O$) δ4.19 (dd, 1H, J=10.9, 3.17 Hz), 4.33 (dd, 1H, J=10.9, 4.66 Hz), 4.75 (m, 1H), 5.48 (d, 1H,J=4.99 Hz), 6.79 (d, 2H, J=8.7 Hz), 7.04 (d, 2H, J=8.7 Hz), 7.25 (m, 3H), 7.34 (d, 2H, J=6.8 Hz), $^{13}$C NMR ($D_2O$) δ66.45 ($CH_2$), 79.42 (CH), 80.12 (CH), 118.62 (CH), 126.79 (C), 128.23 (CH), 129.47 (CH), 129.54 (CH), 130.08 (CH), 136.79 (C), 156.62 (C).

Example 5
Synthesis of 2-Phenoxy-l-phenylethanesulfate, sodium salt (CDDD 1190)

The mother liquor after the crystallization of 2-phenoxy-2-phenylethanol in the synthesis of CDDD 1185 above was evaporated to dryness. Repeated crystallization of the residue from methylene chloride-hexane gave 2-phenoxy-1-phenylethanol as white crystals.

2-phenoxy-1-phenylethanol (5.6 g) isolated as described above was dissolved in dry pyridine (25 ml) and treated with pyridine—$SO_3$ (4.7 g). The mixture was heated with stirring at 70–75° C. for 1 hr. Pyridine was removed in vacuo and the resulting yellow liquid dissolved in water (20 ml). The resulting solution was treated with 1M NaOH solution (about 32 ml) until the pH was 7–8. The water was removed under vacuum to obtain an off-white solid. The solid was extracted with acetonitrile in a Soxhlet to obtain an off-white solid, which was collected and washed with a little acetone, to yield 9.8 g of 2-phenoxy-1-phenylethanesulfate, sodium salt (CDDD 1190), $^1$H NMR ($D_2O$) δ4.18 (m, 2H), 5.48 (m, 1H), 6.77–6.93 (m, 3H), 7.19 (m, 2H), 7.12 (m, 5H), $^{13}$C NMR ($D_2O$) δ70.15 ($CH_2$), 78.0 (CH), 116.1 (CH), 124.2 (CH), 124.0 (CH), 127.1 (CH), 129.9 (CH), 133.8 (C), 156.0 (C).

Example 6
Synthesis of Disodium (2S, 3R)-3-(4-isothiocyanatophenyl)-3-phenoxypropane-1,2-disulfate (1192) and Disodium (2S, 3R)-3-(4-isothiocyanatophenoxy)-3-(4-isothiocyanatophenyl) propane-1,2-disulfate (1193)

Disodium (2S, 3R)-3-(4-isothiocyanatophenyl)-3 phenoxypropane-1,2-disulfate (1192) and Disodium (2S, 3R)-3-(4-isothiocyanatophenoxy)-3-(4-isothiocyanatophenyl)propane-1,2-disulfate (1193) were synthesized according to the general synthetic scheme shown below. Individual synthetic steps are further described in detail.

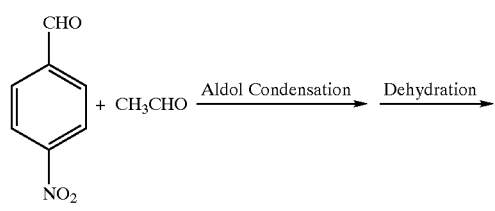
Aldol Condensation / Dehydration
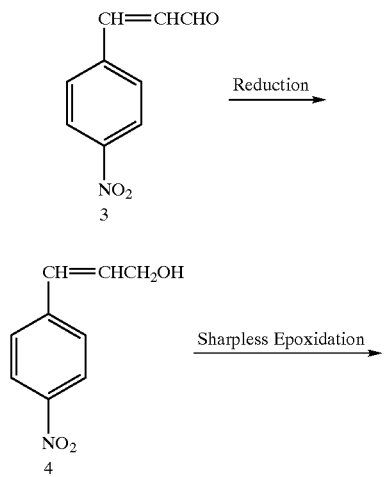
Reduction
Sharpless Epoxidation
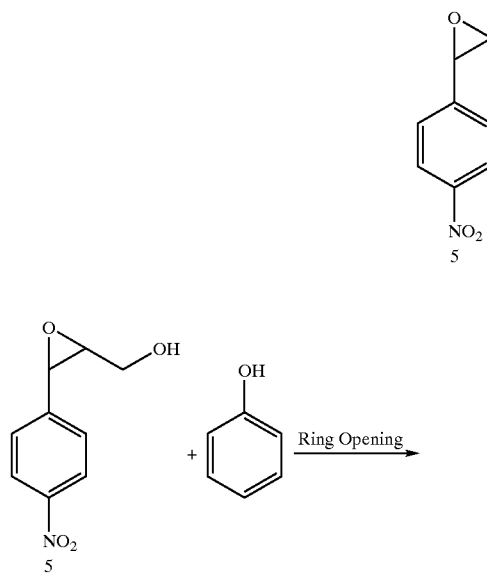
Ring Opening
Sulfation
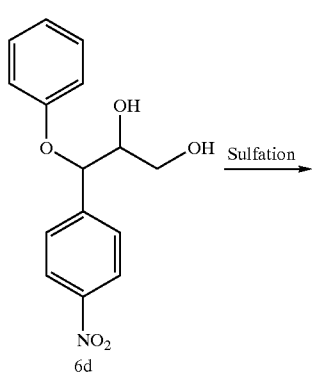
-continued
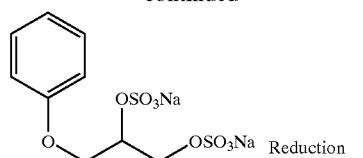
Reduction
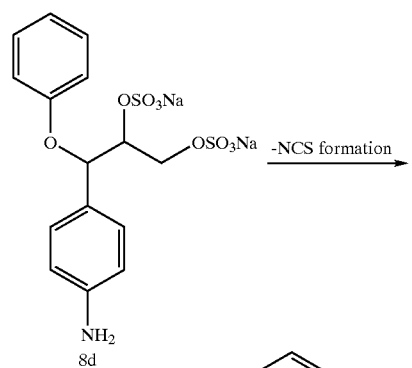
-NCS formation
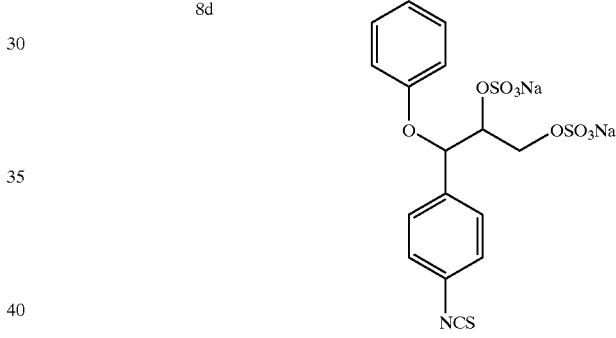
Ring Opening
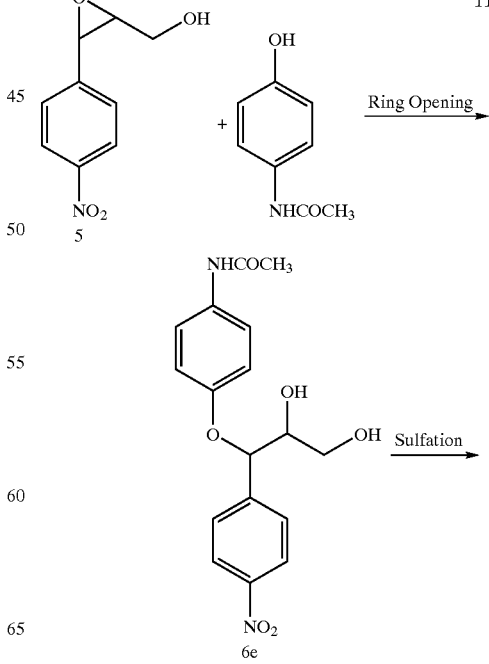
Sulfation

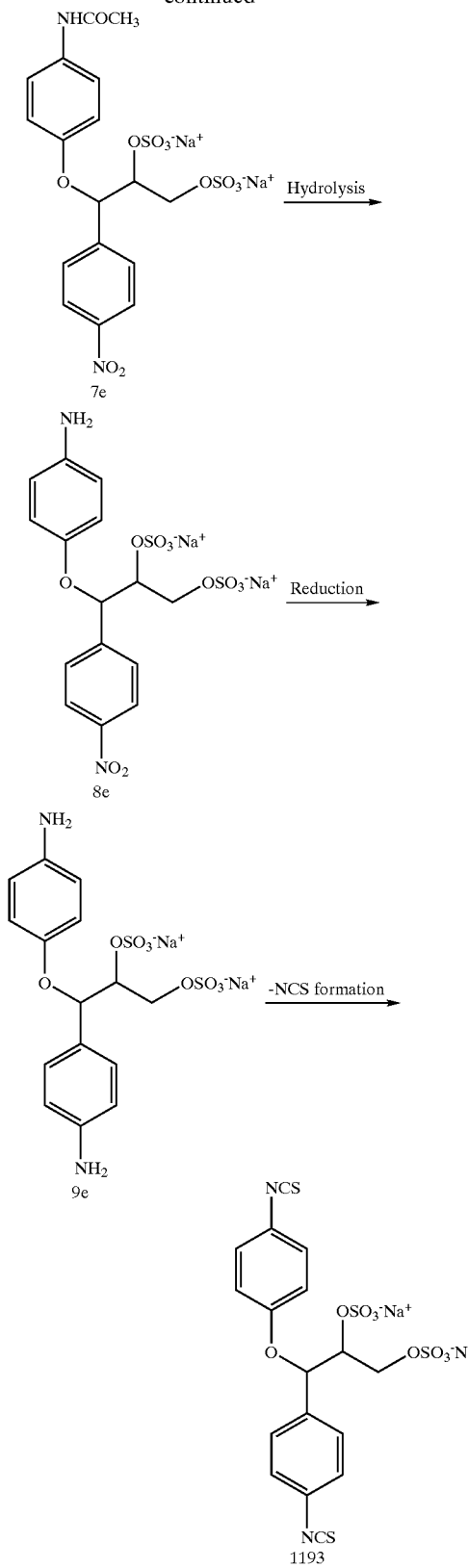

(E)-4-Nitrocinnamaldehyde

In a 300 ml round bottom three-necked flask fitted with a thermometer and dropping funnel were placed 4-nitrobenzaldehyde (25 g, 0.165 mol) and freshly distilled acetaldehyde (50 ml, 0.900 mol). The mixture was stirred and cooled in an ice salt mixture. A 20% solution of potassium hydroxide in methanol was added dropwise to the mixture from the dropping funnel until an alkaline reaction was obtained. During the reaction period (30 min) the reaction mixture was maintained to be alkaline by the addition of more drops of the potassium hydroxide solution. (The total volume of the KOH solution added is about 6 ml). The internal temperature was maintained at 0° C.–5° C. throughout the procedure, which lasted about 40 minutes. At the end of this period, the mixture solidified. If solidification did not occur, stirring was continued until the reaction mixture solidified. Acetic anhydride (80 ml) was added and the mixture was heated for 30 minutes on a steam-bath. The solution was poured into hot water (500 ml) and heated on a steam-bath for 20 minutes after the addition of concentrated hydrochloric acid (32 ml), when yellow needles separated. The mixture was allowed to stand overnight and crystals were collected by filtration under suction and washed with water. Crystallization from methanol-water gave 3 (18.37 g, 62.7%) as pale yellow needles: mp 140–141° C. (literature value: 140–142° C.); $^1$H NMR (400 MHz,CDCl$_3$): δ6.81 (dd, =C—H, J=16 Hz, 7.6 Hz), 7.3) (d,=C—H, J=16 Hz), 7.73 (d, 2H, J=8.8 Hz), 8.29 (d, 2H,=8.8 Hz), 9.78 (d, —CHO, J=7.6 Hz); $^{13}$C NMR (CDCl$_3$): d 192.86(CH), 149.12(C), 148.89(CH), 140.05(C), 131.86(CH), 129.14(CH), 124.45(CH).

(E)-3-(4—Nitrophenyl)-2-propenol (E)-4-Nitrocinnamaldehyde (3,1.0 g, 5.65 mmol) was dissolved in methanol (70 ml ) in a 100 ml flask. Sodium borohydride (106 mg, 2.8 mmol) was added portionwise while stirring. Stirring was continued for 0.5 hr. The solution was evaporated to dryness. The residue was dissolved in a chloroform/water mixture and the organic phase was separated. It was washed twice with distilled water and dried over anhydrous MgSO$_4$. Evaporation of solvent and crystallization from CH$_2$Cl$_2$-hexanes yielded compound 4 (1.0 g, 98%) as a pale yellow solid: mp 129–130° C.; Rf=0.77 (10%CH$_3$OH—CH$_2$Cl$_2$); 1H NMR (300 MHz, CDCl$_3$): δ8.20 (d, aromatic, 2H, J=8.0 Hz), 7.53) (d, aromatic, 2H, J=8.0 Hz), 6.73) (d, 1H, J=16 Hz), 6.57 (m, 1H), 4.20 (d, 2H, J=5.2 Hz), 1.56 (s, 1H); $^{13}$C NMR (CDCl$_3$): δ147.16(C), 143.48(C), 133.81(CH), 128.46(CH), 127.13(CH), 124.23 (CH), 63.30(CH$_2$).

(2S, 3S)-3-(4—Nitrophenyl)oxiranemethanol

A flame-dried 50 ml three-necked flask was fitted with a thermometer and a dropping funnel, flushed with nitrogen, and charged with a mixture of powdered, activated 3 Å molecular sieves (0.45 g) and dry CH$_2$Cl$_2$ (15 ml). After cooling to −5° C., L-(+)-diethyl tartrate (92.8 mg, 0.45 mmol) and Ti(O-i-Pr)$_4$ (88.5 ul, 0.30 mmol) were added sequentially. The mixture was cooled to −20° C. in a CCl$_4$ dry ice bath, (E)-3-(4-nitrophenyl)-2-propenol 4 (1.074 g, 6 mmol) (dissolved in dry methylene chloride (15 ml) and dried with 3Å molecular sieves for 10–15 min prior to addition) was added and the mixture was stirred for 10 minutes. A 7.0 M solution of t-butylhydroperoxide (TBHP) in CH$_2$Cl$_2$ (1.72 ml, 12 mmol) was added, taking care to maintain the temperature around −20° C. After stirring, at −20° C. for 2 hrs, the cold (−20° C.) reaction mixture was quenched with a 10% aqueous solution of sodium hydroxide saturated with sodium chloride (0.48 ml). Ether in the amount of 10% of the total volume of the reaction mixture was added, the cold bath removed and the stirred mixture allowed to warm to 10° C. Stirring was maintained for an additional 10 minutes at 10° C., whereupon anhydrous MgSO$_4$ (0.48 g,) and Celite® (0.06 g) were added. After a final 15 min. of stirring, the mixture was allowed to settle and the clear solution was filtered through a pad of Celite® and washed with ethyl ether. Concentration of the ether solution gave the crude product containing TBHP, which was dissolved in a minimum amount of ethyl acetate, filtered through a small pad of silica gel, and recrystallized from CH$_2$Cl$_2$-hexanes to yield compound 5, (2S, 3S)-3-(4-nitrophenyl) oxiranemethanol (1.13 g, 97%) as light yellow needles: mp 100–101° C. (literature value: 98–99° C.); Rf=0.62 (5% CH$_3$OH—CH$_2$Cl$_2$); 1H NMR (300 MHz, CDCl$_3$) δ: 8.22 (d, aromatic, 2H, J=8.7 Hz), 7.45 (d, aromatic, 2H, J=8.7 Hz), 4.10 (m, 2H) 3.89 (m, 1H), 3.20 (m, 1H), 1.74 (m, 1H); $^{13}$C NMR (CDCl$_3$): d 147.88(C), 144.35(C), 126.41(CH), 123.82(CH), 62.94(CH), 60.62 (CH$_2$), 54.30(CH). Anal. Calcd for C$_9$H$_9$NO$_4$: C, 55.38; H, 4.65; N, 7.18. Found: C, 55–65; H, 4.54; N, 7.17.

(2S, 3R)-3-(4-Nitrophenyl)-3-phenoxypropane-1,2-diol (2S, 3S)-3-(4-nitrophenyl)oxiranemethanol (1.0 g, 5 mmol), phenol (1.41 g, 15 mmol) and methanol (4 ml) were placed in a 25 ml three-necked flask. The resulting solution was heated with stirring at 80° C. on a waterbath. A solution of NaOH (0.24 g, 6 mmol) in H$_2$O (4 ml) was added dropwise and the reaction mixture was heated to gentle reflux (around 80° C.) with stirring for 1.5 hrs. The hot reaction mixture was poured into ice-water containing NaOH (0.6 g in 10 mL of water). The aqueous solution was extracted with ethyl acetate twice. The combined ethyl acetate extract was washed sequentially with dilute NaOH and NaCl solutions, dried over anhydrous Na$_2$SO$_4$ and concentrated in vacuo to give compound 6d (1.36 g, 92%). Rf=0.49 (5% CH$_3$OH—CH$_2$Cl$_2$); $^1$H NMR (300 MHz, CD$_3$OD) δ: 8.19(d, 2H, J=9Hz), 7.67(d, 2H, J=9 Hz), 7.16(d, 2H, J=8 Hz), 6.87(m, 3H), 5.36(d. 2H, J=6 Hz), 4.0(m, 4H), 3.74(m, 1H); $^{13}$C NMR (CD$_3$OD): d 158.87(C), 149.06(C), 147.93(C), 130.57(CH), 130.08(CH), 124.29(CH), 122.51 (CH), 117.16(CH), 80.37(CH), 75.89(CH), 63.82(CH$_2$). Anal. Calcd for C$_{15}$H$_{15}$NO$_5$: C, 62.28; H, 5.23; N, 4.84. Found: C, 62.46; H, 5.30; N, 4.77.

Disodium (2S, 3R)-3-(4-nitrophenyl)-3-phenoxypropane-1, 2-disulfate

Anhydrous pyridine (4 ml) was added to the flask containing the crude product of (2S, 3R)-3-(4-nitrophenyl)-3-phenoxypropane-1,2-diol (0.7 g, 2.5 mmol) from the previous reaction and heated at 60° C. After the crude product dissolved completely in pyridine, sulfur trioxide pyridine complex (1.2 g, 7.5 mmol) was added. The reaction mixture was heated while stirring at 60° C. for 4 hrs, after which it was concentrated to dryness under reduced pressure and the residue dissolved in water. The pH of the solution was adjusted to neutral with 30% aqueous NaOH solution. After extracting with ether twice, the aqueous phase was concentrated to dryness. Inorganic salts were removed by adding methanol and filtering off the solid precipitate. Crystallization from ethanol-ethyl acetate gave 7d (0.92 g, 75%) as white crystals. $^1$H NMR (300 MHz, D$_2$O) d 7.95 (m, 2H, aromatic), 7.50 (m, 2H, aromatic), 7.05 (m, 2H, aromatic), 6.80 (m, 3H, aromatic), 5.55 (m, 1H), 4.65 (m, 1H), 4.30 (m, 2H); $^{13}$C NMR (in D$_2$O; CD$_3$OD was used as an internal reference): δ157.52(C), 148.51(C), 145.36(C), 130.69(CH), 129.68(CH), 124.59(CH), 123.12(CH), 117.37(CH), 79.32 (CH), 77.69(CH), 66.65(CH$_2$).

Disodium (2S, 3R)-3-(4-aminophenyl)-3-phenoxypropane-1,2-disulfate

Disodium (2S, 3R)-3-(4-nitrophenyl)-3-phenoxypropane-1,2-disulfate (500 mg, 1.0 mmol) was dissolved in MeOH (12 ml) and a saturated solution of Cu(OAc)$_2$ (4 ml) was added. Sodium borohydride (400 mg, 10 mmol) was added in small portions with stirring, at room temperature. After 2.5 hrs, the reaction mixture was filtered. Concentration of the filtrate and crystallization from ethanol yielded the crude product of 8d (470 mg), which contained some sodium acetate. $^1$HNMR (300 MHz, D$_2$O) δ7.10 (m, 4H), 6.85 (m, 3H), 6.65 (m, 2H), 5.40 (d, 1H), 4.20 (m, 2H); $^{13}$C NMR (in D$_2$O; CD$_3$OD was used as an internal reference): δ158.12 (C), 147.45(C), 130.72(CH), 129.70(CH), 127.78(CH), 122.84(CH), 117.64(CH), 117.35(CH), 80.29(CH), 79.10 (CH), 66.79(CH$_2$).

Disodium (2S, 3R)-3-(4-isothiocyanatophenyl)-3-phenoxypropane-1,2-disulfate (1192)

To a solution of the crude product (300 mg) of Disodium (2S, 3R)-3-(4-aminophenyl)-3-phenoxypropane-1,2-disulfate from the previous step in 1% NaCl solution (1 ml) was added thiophosgene (157 ml, 2.0 mmol). After vigorous stirring at r.t. for 1.5 hrs, the excess thiophosgene was removed by washing several times with ether. Tetrahydrofuran (THF) (1 ml) was added to the aqueous solution with shaking. Concentration of the organic THF phase yielded 1192 as a white powder (100 mg). The total yield of the last two steps was 30%. IR (KBr): 3500, 2200, 1600, 1250, 1000, 900 cm-1; $^1$H NMR (300 MHz, D$_2$O): δ7.36(m, 2H), 7.10(m, 4H), 6.85(m, 3H), 5.50(d, 1H), 4.10(m, 2H); $^{13}$C NMR (in D$_2$O; CD$_3$OD was used as an internal reference): δ157.11(C), 136.29(C), 134.81(C), 131.04(C), 130.14(CH), 129.31(CH), 126.18(CH), 122.45(CH), 116.89(CH), 79.04 (CH), 77.57(CH), 66.05(CH$_2$).

(2S, 3R)-3(4-Acetamidophenoxy)-3-(4-nitrophenyl) propane-1,2-diol (2S, 3S)-3-(4-nitrophenyl)oxiranemethanol (5)(2.5 g, 12.8 mmol), 4-acetamidophenol (5.8 g, 38.4 mmol) and methanol (20 ml) were placed in a 100 ml three-necked flask. The resulting solution was heated with stirring at 80° C. on a water-bath. A solution of NaOH (0.6 g, 15 mmol) in H$_2$O (20 ml) was added and the reaction mixture was heated to reflux with stirring for 2 hrs. The hot reaction mixture was poured into ice-water (100 ml) containing NaOH (2 g) and extracted with ethyl acetate twice. The combined ethyl acetate extract was washed sequentially with dilute NaOH and NaCl solutions, dried over anhydrous Na$_2$SO$_4$ and concentrated to give the crude product. Crystallization from methylene chloride yielded pale yellow crystals of compound 6e (4.05 g, 91.2%): mp 110–111° C.; Rf=0.47 (10% CH$_3$OH—CH$_2$Cl$_2$); $^1$H NMR (300 MHz, CD$_3$OD): δ8.15 (d, 2H), 7.65(d, 2H), 7.30(d, 2H), 6.80(d, 2H), 5.30(d, 1H), 4.00(m, 1H), 3.70(m, 2H), 2.00(s, 3H); $^{13}$C NMR (CD$_3$OD): δ171.41(C), 155.37(C), 148.99(C), 147.72(C), 133.53(C), 130.04(CH), 124.17(CH), 122.90(CH), 117.26(CH), 80.67 (CH), 75.71(CH), 63.69(CH$_2$), 23.52(CH$_3$). Calcd for C$_{17}$H$_{18}$N56.02; H, 5.54; N, 7.69. Found: C, 56.21; H, 5.67; N, 7.34.

Disodium (2S, 3R)-3-(4-acetamidophenoxy)-3-4-nitrophenyl)propane-1,2-disulfate

A mixture of (2S, 3R)-3-(4-acetamidophenoxy)-3-(4-nitrophenyl)propane-1,2-diol (1.04 g, 3 mmol) and anhydrous pyridine (5 ml) was heated with stirring, at 60° C. in a 50 ml flask and sulfur trioxide pyridine complex (1.91 g, 12.0 mmol) was added to the resulting solution. The reaction mixture was heated with stirring at 60° C. for 8 hrs, after which it was concentrated to dryness under reduced pressure and the residue dissolved in water. The pH of the solution was adjusted to neutral with 30% aqueous NaOH solution. After extracting with ether twice, the aqueous phase was concentrated to dryness. Inorganic salts were removed by adding methanol and filtering off the solid precipitate. Concentration of the filtrate gave the crude product of 7e, which was used directly in the following hydrolysis reaction. $^1$H NMR (300 MHz, $D_2O$): δ7.80(d. 2H), 7.30(d, 2H), 7.00(d, 2H), 6.65(d, 2H), 5.40(d, 2H), 4.25(m, 2H), 1.95(s, 3H); $^{13}$C NMR (in $D_2O$; $CD_3OD$ was used as an internal reference): δ173.54(C), 154.92(C), 148.37(C), 145.36(C), 132.27(C), 129.65(CH), 124.60(CH), 124.26(CH), 117.76(CH), 79.46 (CH), 78.05(CH), 66.71($CH_2$), 23.72($CH_3$).

Disodium (2S, 3R)-3-(4-aminophenoxy)-3-(4-nitrophenyl) propane-1,2-disulfate

The crude product of Disodium (2S, 3R)-3-(4-acetamidophenoxyl)3-(4-nitrophenyl)propane-1,2-disulfate from the previous reaction and 10% aqueous NaOH (5 ml) solution were placed into a 25 ml flask. After stirring at 40° C. for 4 days, the pH of the mixture was adjusted to 8 with 1N $H_2SO_4$ and the solution was concentrated to dryness. After removing $Na_2SO_4$ by adding methanol and filtration, concentration of the filtrate and crystallization from ethanol yielded 8e as a pure pale red solid. The total yield of the two steps was 42.2%. $^1$H NMR (300 MHz, $D_2O$): δ7.85(d, 2H), 7.40(d, 2H), 6.70(d. 2H), 6.50(d, 2H), 5.35(d, 1H), 4.25(m, 2H); $^{13}$C NMR (in $D_2O$; $CD_3OD$ was used as an internal reference): δ151.46(C), 148.70(C), 145.91(C), 141.86(C), 130.00(CH), 124.67(CH), 119.15(CH), 118.64(CH), 79.43 (CH), 79.37(CH), 66.74($CH_2$). Anal. Calcd for $C_{15}H_{14}N_2O_{11}S_2Na_2$: C, 35.44; H, 2.78; N, 5.51. Found: C, 35.41; H, 3.20; N, 5.07.

Disodium (2S, 3R)-3-(4-aminophenoxy)-3-(4-aminophenyl) propane-1,2-disulfate

Disodium (2S, 3R)-3-(4-aminophenoxy)-3-(4-nitrophenyl)propane-1,2-disulfate (300 mg, 0.59 mmol), CuCl (292 mg, 2.95 mmol) and ethanol (15 ml) were added to a 25 ml flask and the resulting mixture was stirred at r.t. After $NaBH_4$ (222 mg, 5.9 mmol) was added in three portions, the reaction mixture was heated to reflux with stirring for 1 hr and filtered. The filtrate was concentrated to dryness and dissolved in minimum amount of water. Extraction of the resulting aqueous solution with acetonitrile three times gave the product 9e (160 mg, 57%) after concentration. $^1$H NMR (300 MHz, $D_2O$): δ7.08(d, 2H), 6.65(m, 4H), 6.50(m, 2H), 5.22(d. 1H), 4.20(m, 2H); $^{13}$C NMR (in $D_2O$; $CD_3OD$ was used as an internal reference): δ151.79(C), 147.40(C), 141.36(C), 129.78(CH), 128.04(C), 119.20(CH), 118.64(CH), 117.15(CH), 80.53(CH), 80.29(CH), 66.80 ($CH_2$).

Disodium (2S, 3R)-3-(4-isothiocyanophenoxy)-3-(4-isothiocyanatophenyl)propane-1,2-disulfate (1193)

Thiophosgene (128 ml, 16 mmol) was added to a solution of disodium (2S, 3R)-3-(4-aminophenoxy)-3-(4-aminophenyl)-3-(4-aminophenyl)propane-1,2-disulfate (200 mg, 0.4 mmol) and NaOAc (137 mg, 1.6 mmol) in water (300 ml) and the mixture was stirred vigorously for 1 hr. After repeated extraction with ether, the pH of the aqueous reaction mixture was adjusted to 7 with 1N NaOH solution. Extraction of the neutral aqueous solution with acetonitrile twice and concentration yielded compound 1193 (164 mg, 70%) as a powder: mp 195–196° C.(decomp.); IR(KBr): 3456, 2116, 1604, 1501, 1236, 1032, 924, 827 cm-1; $^1$H NMR (300 MHz, $D_2O$): δ7.32(d, 2H, J=8.4 Hz), 7.09(d. 2H, J=8.4 Hz), 6.93(d. 2H, J=8.9 Hz), 6.76(d. 2H, J=8.9 Hz), 5.46(d. 1H, J=5.9 Hz), 4.26(m, 2H); $^{13}$C NMR (in $D_2O$; $CD_3OD$ was used as an internal reference): δ156.81 (C), 136.49(C), 135.72(C), 134.11(C), 131.79(C), 129.92 (CH), 127.96(CH), 126.90(CH), 124.95(C), 118.30(CH), 79.68(CH), 78.39(CH), 66.70($CH_2$). Calcd for $C_{17}H_{12}N_2O_9S_4Na_2 \cdot 2H_2O$ (the presence of water of crystallization is also indicated by the infrared spectrum): C, 34.11; H, 2.69; N, 4.68; S, 21.43. Found: C, 34.27; H, 2.61; N, 4.77; S, 21.25.

Synthesis of other Stereoisomers of 1193

(2R, 3S)-1193 may be synthesized as above, replacing L-(+)-diethyl tartrate with D-(-)-diethyl tartrate in the synthesis of 3-(4-nitrophenyl) oxiranemethanol (5).

(2S, 3S)-1193 maybe synthesized as above, replacing (E)-4-nitrocinnamaldehyde with (Z)-4-nitrocinnamaldehyde, and using L-(+)-diethyl tartrate in the synthesis of 3-(4-nitrophenyl) oxiranemethanol (5). (Z)-4-nitrocinnamaldehyde may be synthesized according to the method in Daubresse, N., et al. (*Tetrahedron* 54(360): 10761–10770, 1998).

(2R, 3R)-1 193 may be synthesized as above, replacing (E)-4-nitrocinnamaldehyde with (Z)-4-nitrocinnamaldehyde and replacing L-(+)-diethyl tartrate with D-(-)-diethyl tartrate in the synthesis of 3-(4-nitrophenyl) oxiranemethanol (5).

Example 7

Ussing Chamber Method For Assessing Esophageal Epithelial Protection Against Acid Injury Previously, a test system was developed in the Ussing chamber to identify and characterize agents with cytoprotective effects against acid injury to the tissue. Briefly, the esophageal epithelium is mounted in the Ussing chamber so that acid (or acid-pepsin) could be added to the luminal bath while monitoring changes in electrical resistance (R). The changes in R are an effective means to identify damage by acid or acid-pepsin since damage is heralded by an increase in paracellular permeability and this reflected by a decline in R. In effect, the ability of an agent or compound to prevent the acid-induced decline in R without altering luminal pH (which excludes protection being mediated by acid buffering or neutralization) is evidence for a cytoprotective effect, i.e. protection directly exerted by the agent or compound on the epithelium. Further, we previously established that the ability of an agent or compound to prevent the acid-induced decline in R in this Ussing chamber model of acid injury was an accurate predictor, and therefore surrogate marker, of its ability to protect rabbit esophageal epithelium against acid injury in vivo (U.S. Pat. Nos. 5,374,537 and 5,189,056).

New Zealand white rabbits weighing between 8–9 lbs are sacrificed by administering an intravenous overdose of phenobarbital (60 mg/mL). The esophagus is excised, opened, and pinned mucosal surface down in a paraffin tray containing ice-cold oxygenated normal Ringer's solution. The submucosa is grasped with hemostats, lifted up, and dissected free of the underlying mucosa with a scalpel. This process yields a sheet of tissue consisting of stratified squamous epithelium and a small amount of underlying connective tissue. From this tissue, four sections are cut and mounted as flat sheets between Lucite half-chambers with an aperture of 1.13 $cm^2$ for measurements of potential difference (PD), short circuit current (Isc) and, from these values, calculation of transmucosal electrical resistance (R). Tissues are bathed with normal Ringer solution composed of the following (in mmol/L): Na 140; Cl 119.8; K 5.2; $HCO_3$ 25; Ca 1.2; Mg 1.2; $HPO_4$ 2.4; $H_2PO_4$ 0.4; and 268 mOsm/kg water, with pH 7.5 when gassed with 95% $O_2$/5% $CO_2$ at 37° C. Mucosal and serosal solutions are connected to calomel and Ag—AgCl electrodes with Ringer's-agar bridges for measurements of PD and automatic short-circuiting of the tissue with a voltage clamp (World Precision Instruments Inc., Sarasota, Fla.). Tissues are monitored continuously in the open-circuit state except for 5–10 second periods when the Isc is read. Electrical resistance (R) was calculated using Ohm's Law from the open-circuit PD and Isc.

To test the protective effect of an agent against acid injury to esophageal epithelium, 45 minutes after mounting (equilibration period), tissues paired by R had for one of the pair varying amounts of an agent added to the luminal bath while the other part of the pair received vehicle (normal Ringer solution) as control. After varying periods of exposure to the agent, 60 mM HCl was added to the luminal (mucosal) solution to reduce pH to 1.6; the pH was monitored and maintained throughout the 1 hr of exposure for all tissues to ensure uniform risk of injury. This negated any protective effect as being due to buffering by the agent. In some experiments the power of the protective effect of an agent was determined after varying periods of luminal exposure by washout prior to acid exposure, i.e. replacement of the luminal bath containing agent with normal Ringer Solution that contained only vehicle. R was then monitored before and during acidification with 60 mM HCl and the results for agent and controls presented as percent decline in R from pre-acidification values. Since the human esophagus in vivo is never exposed to such high concentrations of HCl for such long periods (i.e. exposures to this pH last <1 min), the ability of a test agent to provide even small (statistically significant) differences from that of control against such acidity can effectively translate into a clinically important beneficial effect in humans with a reflux disease, such as GERD. Finally, junction potentials develop during luminal exposure to 60 mM HCl in the Ussing chamber, but since these potentials alter both PD and Isc, they are factored out and so do not interfere with the accurate determination of R.

FIG. 1 is a graph showing the dose-dependent protective effect of 4-acetamido-4'-isothiocyanatostilbene-2-2'-disulfonic acid (SITS). Rabbit esophageal epithelium mounted in Ussing chambers is exposed luminally to different doses of SITS or to vehicle alone (normal Ringer solution) for 30 min prior to the luminal addition of 60 mM HCl, pH 1.6, for 1 hour. Electrical resistance, R, is monitored and at the end of the 1 hour of acid exposure, the value for R is calculated as percent (%) of the initial R for the tissue. The Figure shows that the lowest protective dose of SITS even while remaining continuously in the bath during acid exposure is 0.1 mM. N=4 tissues/dose; $*p<0.05$ compared to controls.

Figure 2:
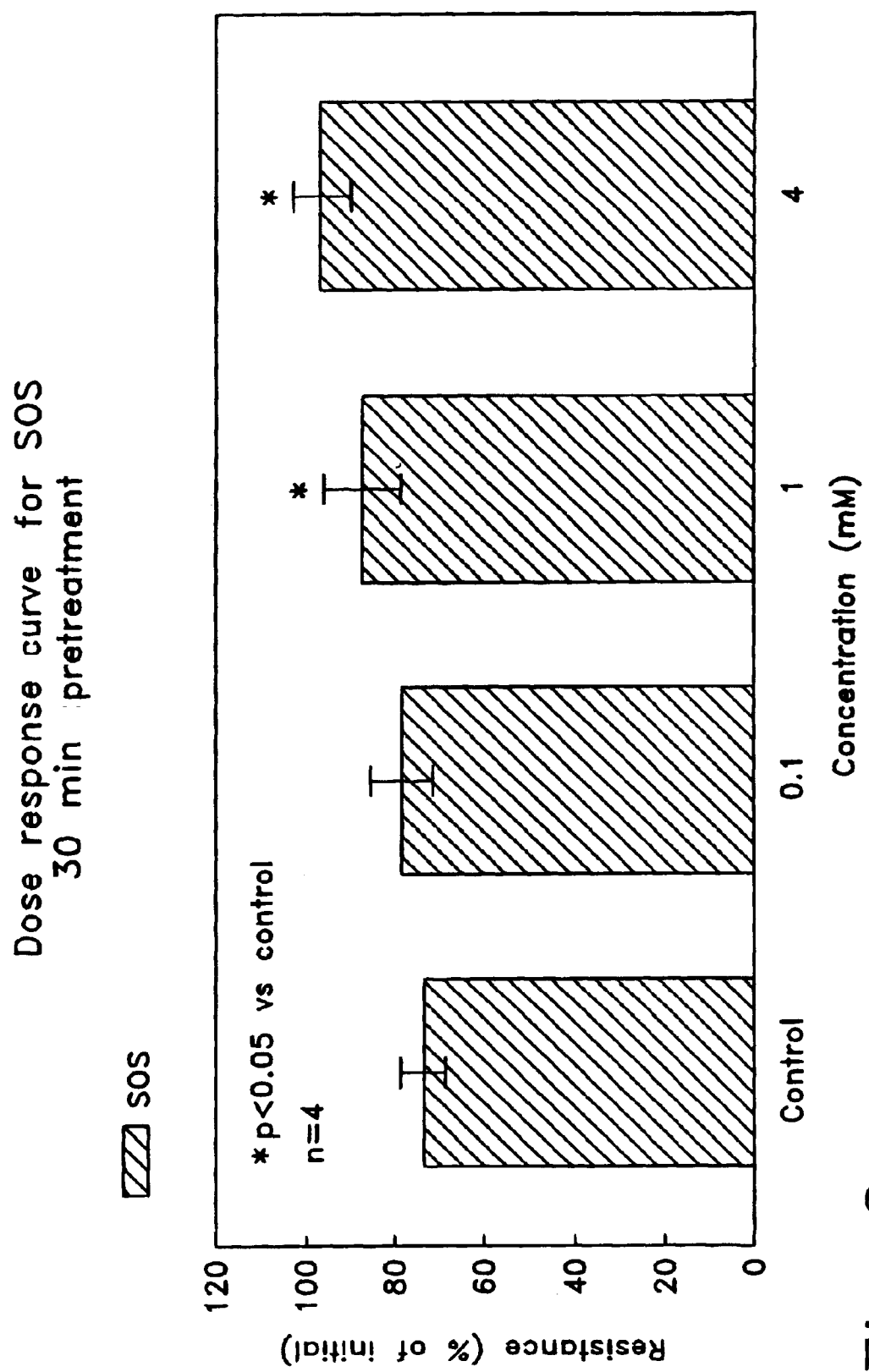
FIG. 2 is a graph showing the dose-dependent protective effect of sucrose octasulfate (SOS).

FIG. 2 is a graph showing the dose-dependent protective effect of sucrose octasulfate (SOS). Different doses of SOS were tested as in FIG. 1. The Figure shows that the lowest protective dose of SOS even with SOS remaining in the luminal bath during acid exposure is 1 mM. N=4 tissues/dose; $*p<0.05$ compared to controls.

Figure 3:
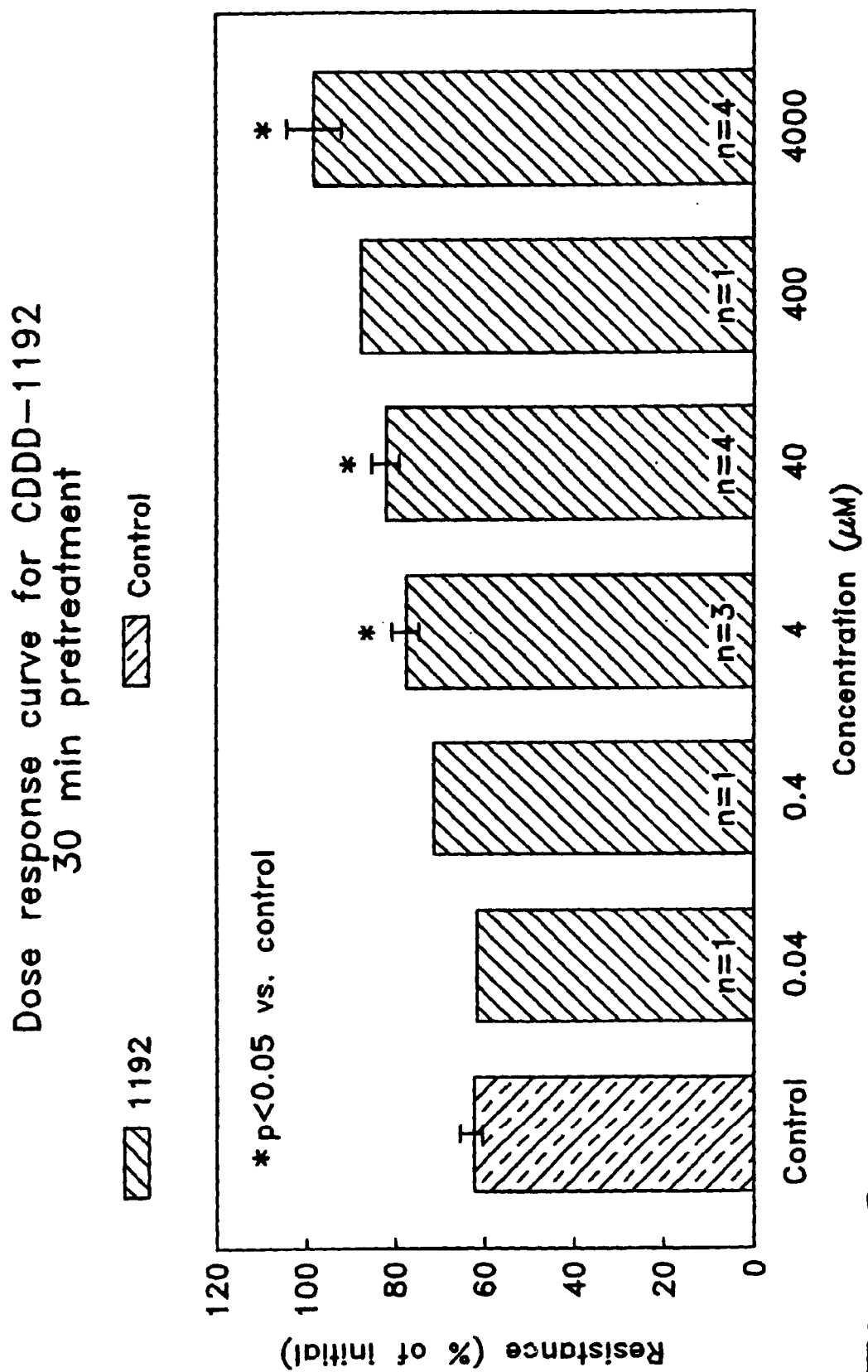
FIG. 3 is a graph showing the dose-dependent protective effect of a novel sulfate ester of the invention (CDDD-1192).

FIG. 3 is a graph showing the dose-dependent protective effect of CDDD-1192. Different doses of CDDD-1192 were tested as in FIG. 1. The Figure shows that the lowest protective dose of CDDD-1192 while remaining in the luminal bath during acid exposure is 4 $\mu$M. N=1–4 tissues/dose (see each bar for N); $*p<0.05$ compared to controls.

Figure 4:
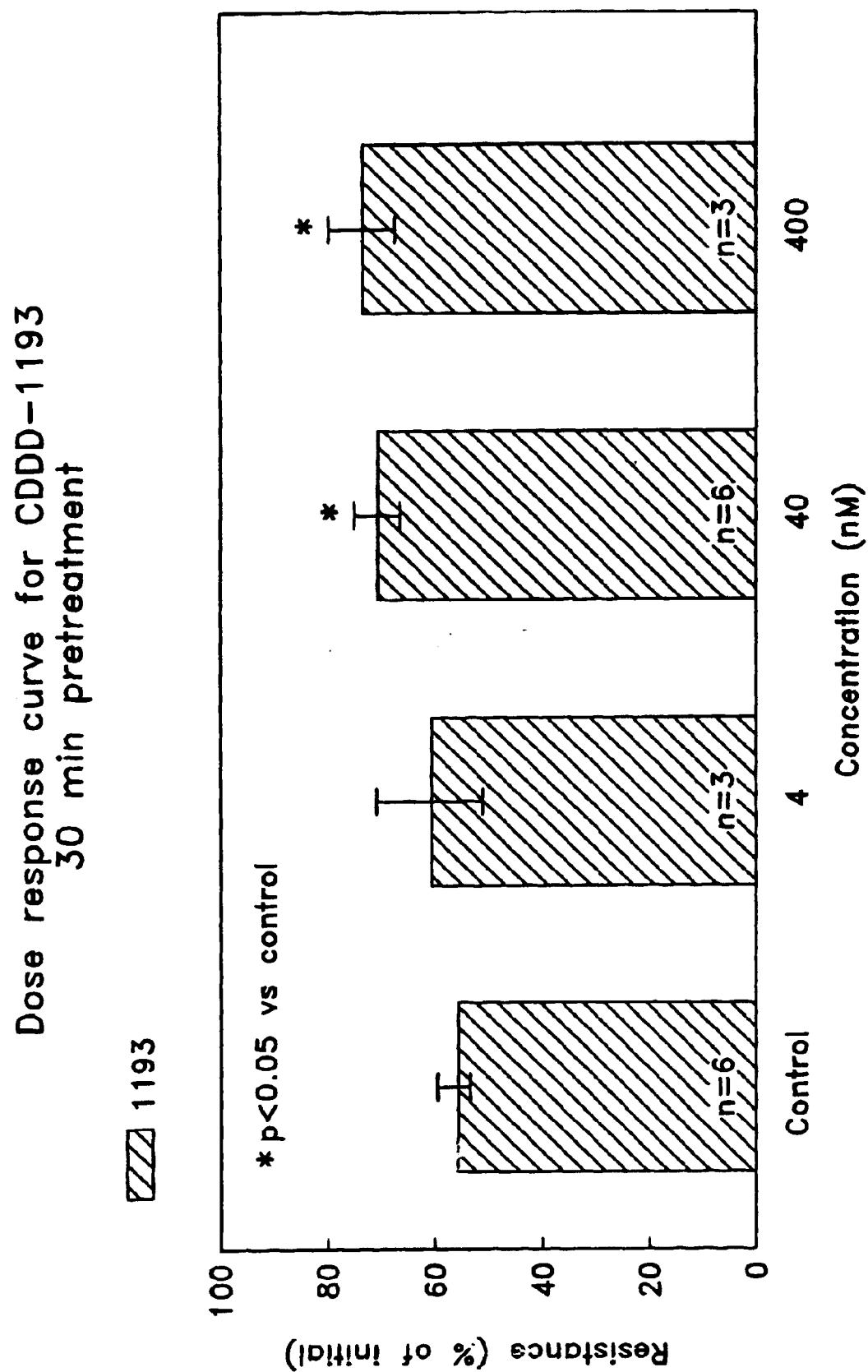
FIG. 4 is a graph showing the dose-dependent protective effect of another novel sulfate ester of the invention (CDDD-1193).

FIG. 4 is a graph showing the dose-dependent protective effect of CDDD-1193. Different doses of CDDD-1193 were tested as in FIG. 1. The Figure shows that the lowest protective dose of CDDD-1193 while remaining in the luminal bath during acid exposure is 40 nM. N=3–6 tissues/dose (see each bar for N); $*p<0.05$ compared to controls.

Figure 5:
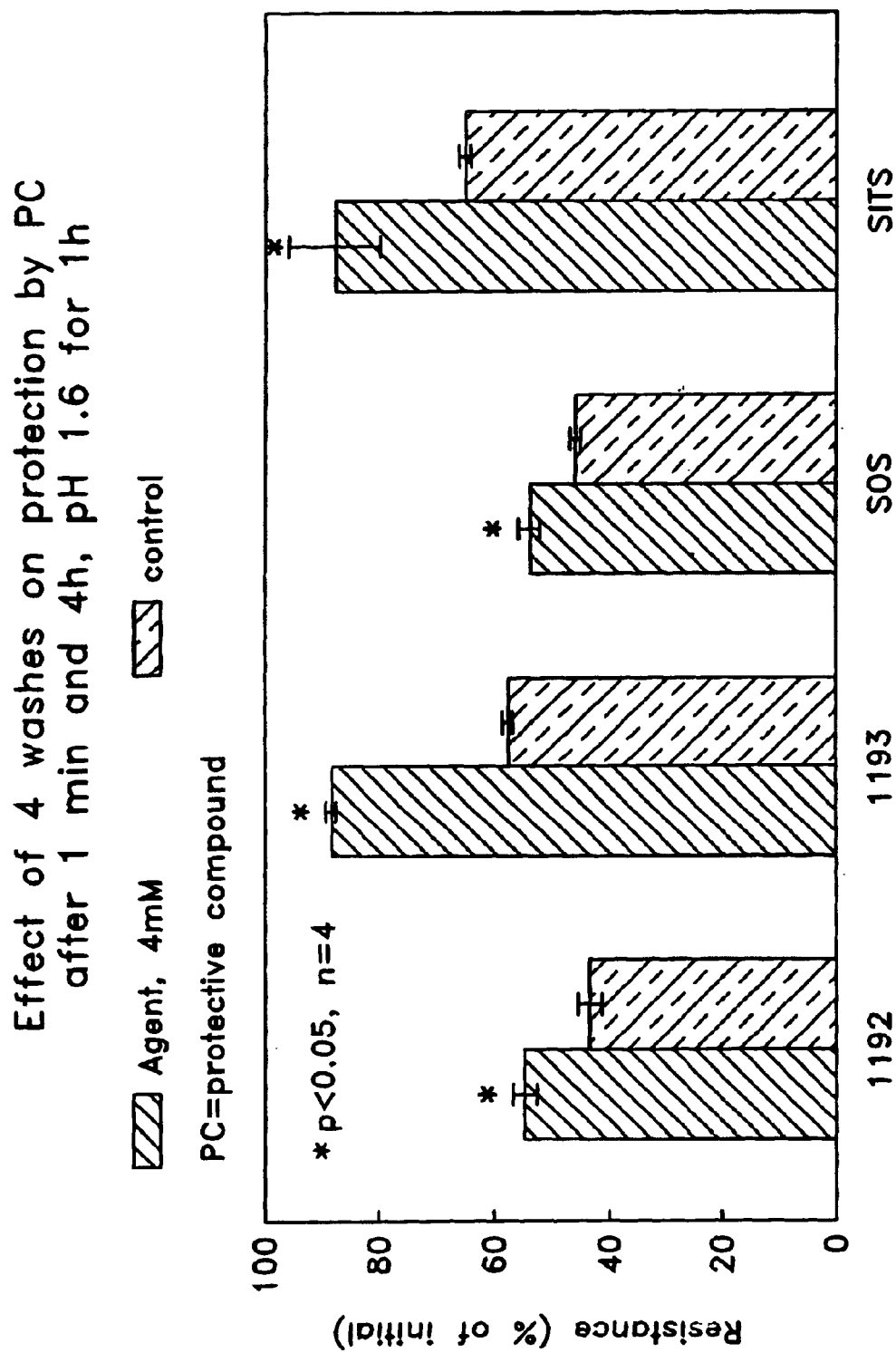
FIG. 5 is a graph showing a comparison of protection against acid injury to esophageal epithelium of SOS, SITS, CDDD-1192 and CDDD-1193 after brief luminal exposure.

FIG. 5 is a graph showing a comparison of protection against acid injury to esophageal epithelium for SOS, SITS, CDDD-1192 and CDDD-1193 after brief luminal exposure. Rabbit esohageal epithelium mounted in Ussing chambers is exposed luminally for 1 min to a similar dose (4 mM) of a protective agent, i.e. SITS, SOS, CDDD-1192, or CDDD-1193 or to vehicle alone (normal Ringer solution), and then the tissue is subjected to multiple washouts over a 4 hour period prior to the luminal addition of 60 mM HCl, pH 1.6, for 1 hour. Electrical resistance, R, is monitored and at the end of the 1 hour of acid exposure, the value for R is calculated as percent (%) of the initial R for the tissue. The Figure shows that all the agents retain significant protection even with brief exposures and multiple washouts. The durability of the protection suggests that these may have clinical utility. N=4 tissues/dose (see each bar for N); $*p<0.05$ compared to controls.

Figure 6:
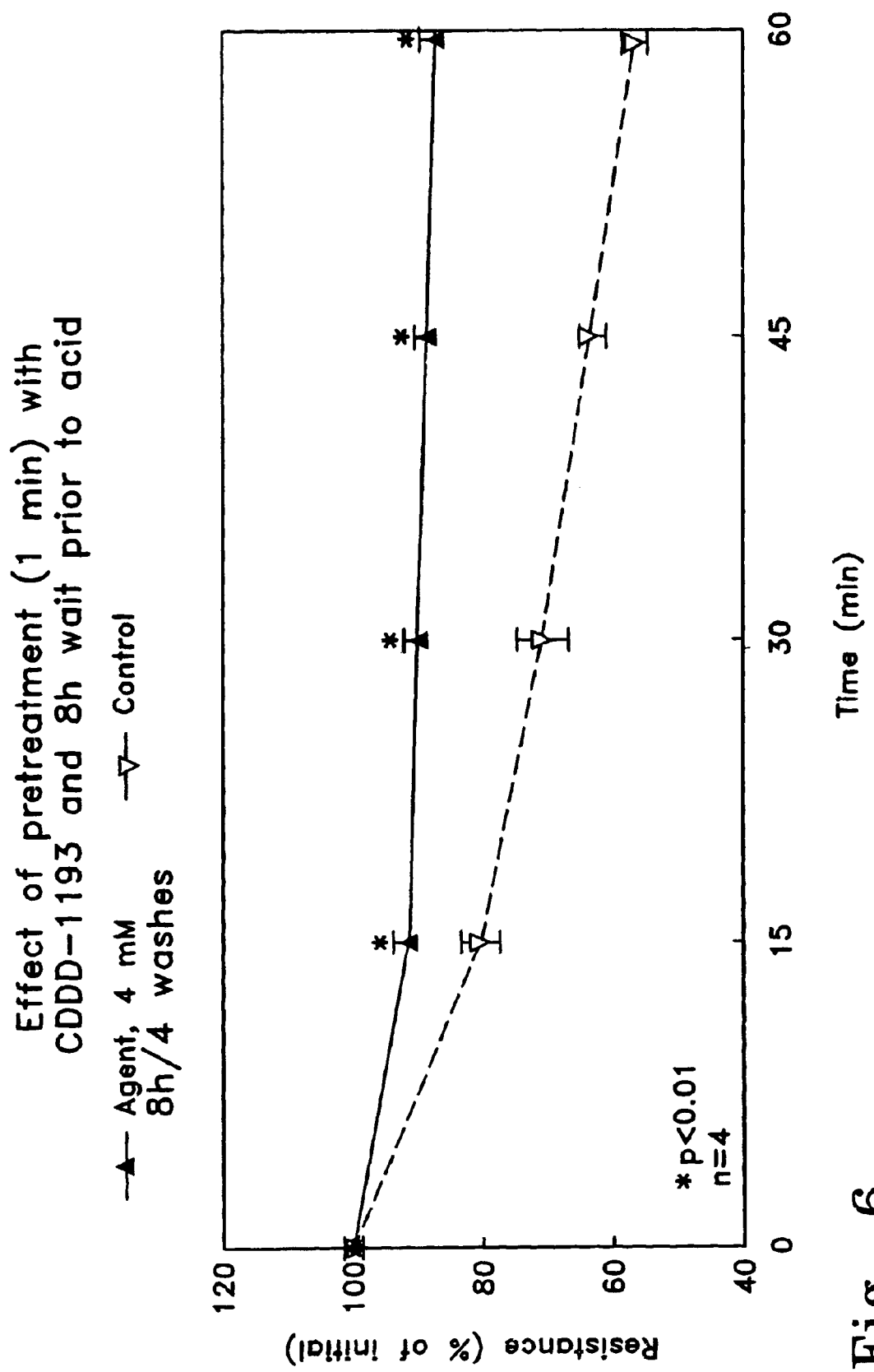
FIG. 6 is a graph showing the protective effect of CDDD-1193 after brief luminal exposure.

FIG. 6 is a graph showing the protective effect of CDDD-1193 after brief luminal exposure. Rabbit esophageal epithelium mounted in Ussing chambers is exposed luminally for 1 min to 4 mM CDDD-1193 or to vehicle alone (normal Ringer solution), and then the tissue is subjected to multiple washouts over an 8 hour period prior to the luminal addition of 60 mM HCl pH 1.6, for 1 hour. Electrical resistance, R, is monitored and plotted as percent initial R (%) every 15 min for the 1 hour of acid exposure. The Figure shows that the protective effect of CDDD-1193 against 1 hr of exposure to high concentrations of acid is substantial and persists for 8 hrs even with only brief (1 min) exposure and vigorous attempts to reverse the effect by repeated washes. N=4 tissues/dose (see each bar for N); $*p<0.05$ compared to controls.

Figure 7:
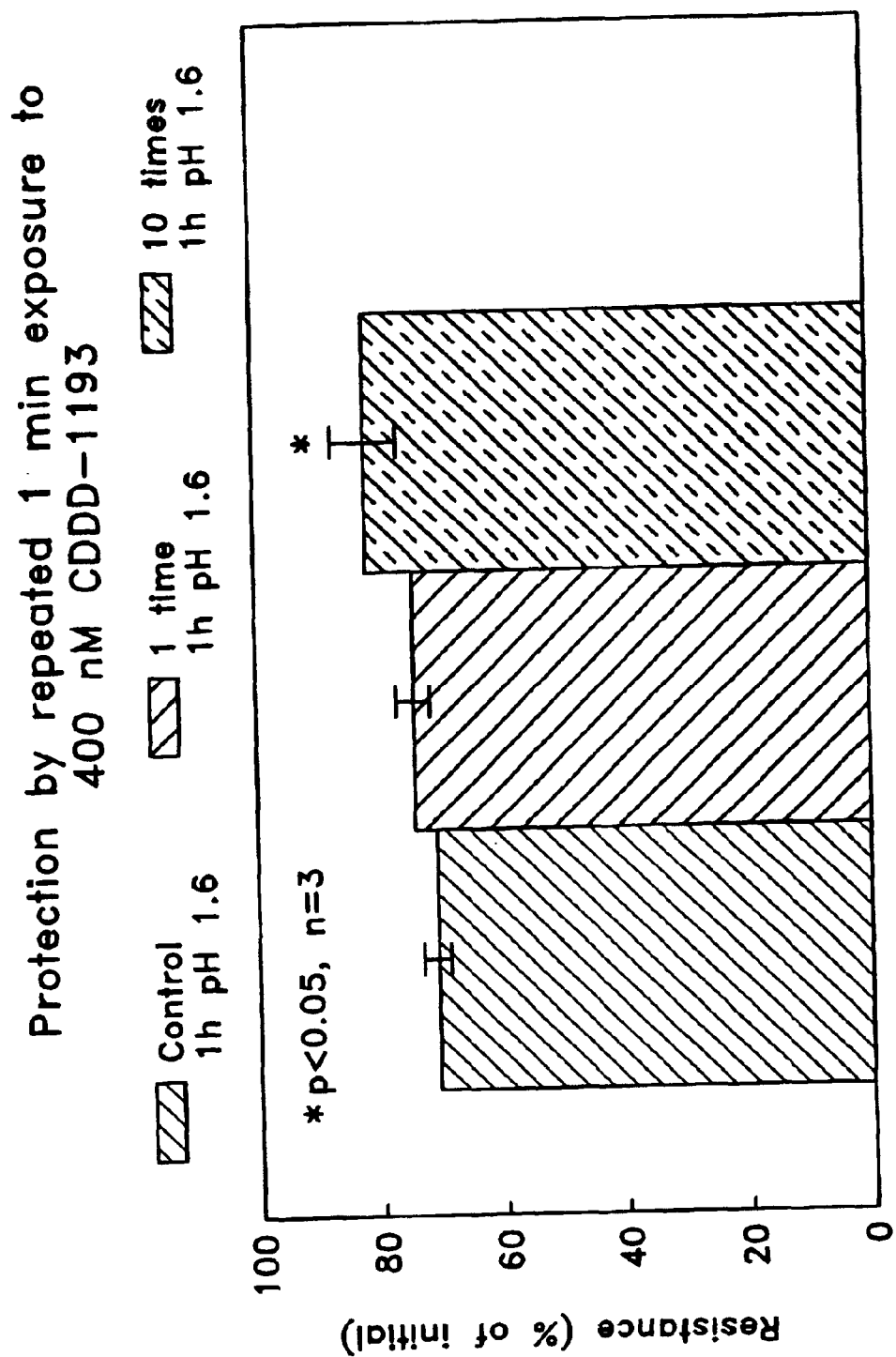
FIG. 7 is a graph showing the cumulative protective effect of 400 nM CDDD-1193 for esophageal protection after repeated brief exposures.

FIG. 7 is a graph showing the cumulative protective effect of 400 nM CDDD-1193 for esophageal protection after repeated brief exposures. Rabbit esophageal epithelium mounted in Ussing chambers is exposed luminally to 400 nM CDDD-1193 for 1 min once or for 1 min every 5 min times ten exposures or to vehicle alone (normal Ringer solution) prior to the luminal addition of 60 mM HCl, pH 1.6, for 1 hour. Electrical resistance, R, is monitored and plotted at the end of 1 hour of acid exposure as percent (%) of the initial R for the tissue. The Figure shows that while a single 1 min exposure to 400 nM CDDD-1193 has little protection, repeated exposures to the same concentration are protective against high concentrations of HCl for 1 hr. This suggests that the protective effects of CDDD-1193 are cumulative with repeated dosing as would occur with multiple swallows in vivo in humans drinking a liquid preparation of agent. N=3 tissues/dose; $*p<0.05$ compared to controls.

Figure 8:
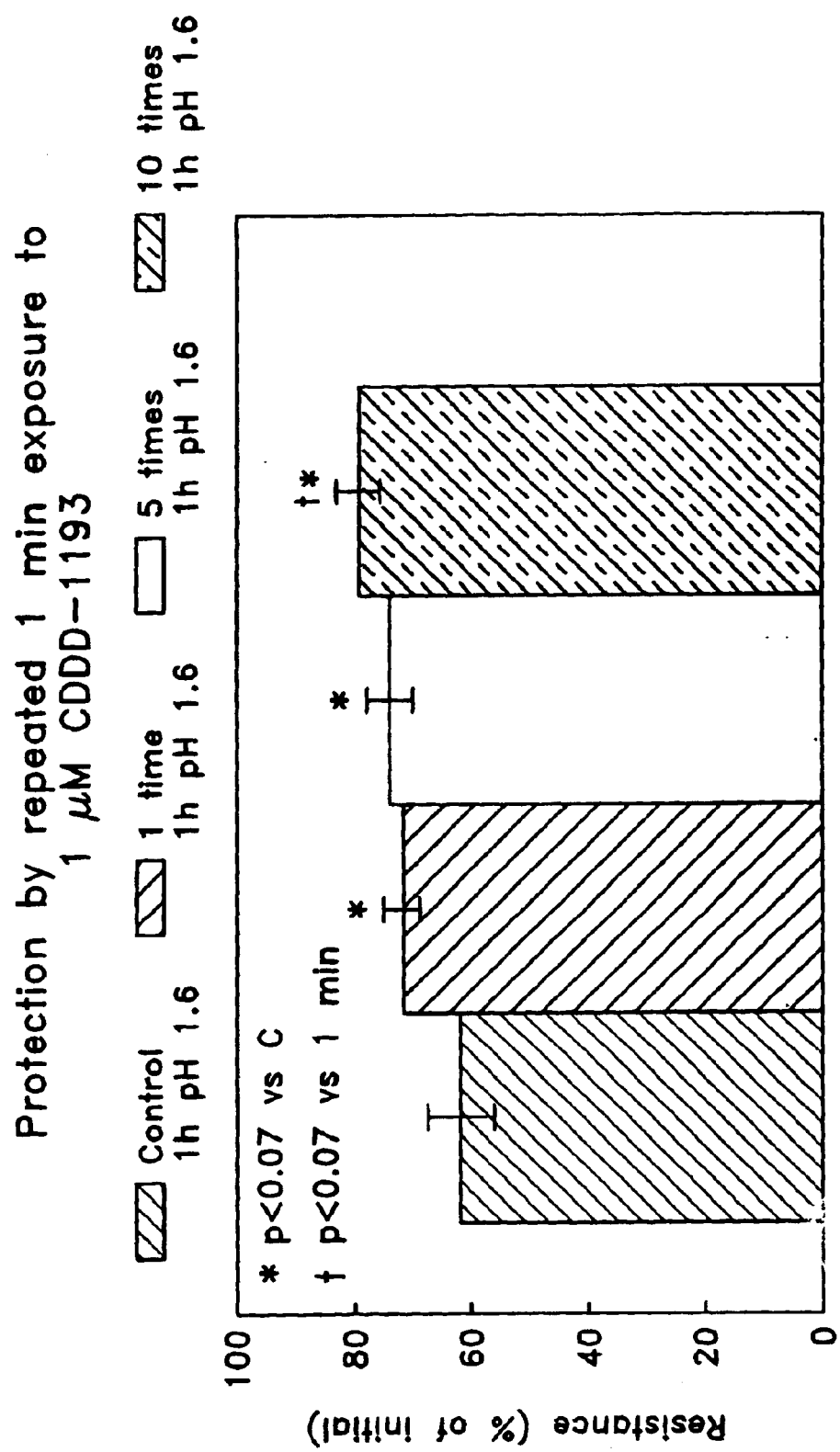
FIG. 8 is a graph showing the cumulative protective effect of 1 μM CDDD-1193 for esophageal protection after repeated brief exposures.

FIG. 8 is a graph showing the cumulative protective effect of 1 $\mu$M CDDD-1193 for esophageal protection after repeated brief exposures. 1 $\mu$M doses of CDDD-1193 were tested as in FIG. 7 for 1 min once, for 1 min every 5 min times 5 exposures, or for 1 min every 5 min times ten exposures. The Figure shows that a single 1 min exposure to 1 $\mu$M CDDD-1193 is modestly protective and that this protective effect is cumulative with repeated exposures. Note that the higher degree of protection shown for ten exposures approaches statistical significance over that for 1 exposure to the agent, with $p<0.07$. N=4 tissues/dose; $*p<0.05$ compared to controls.

Figure 9:
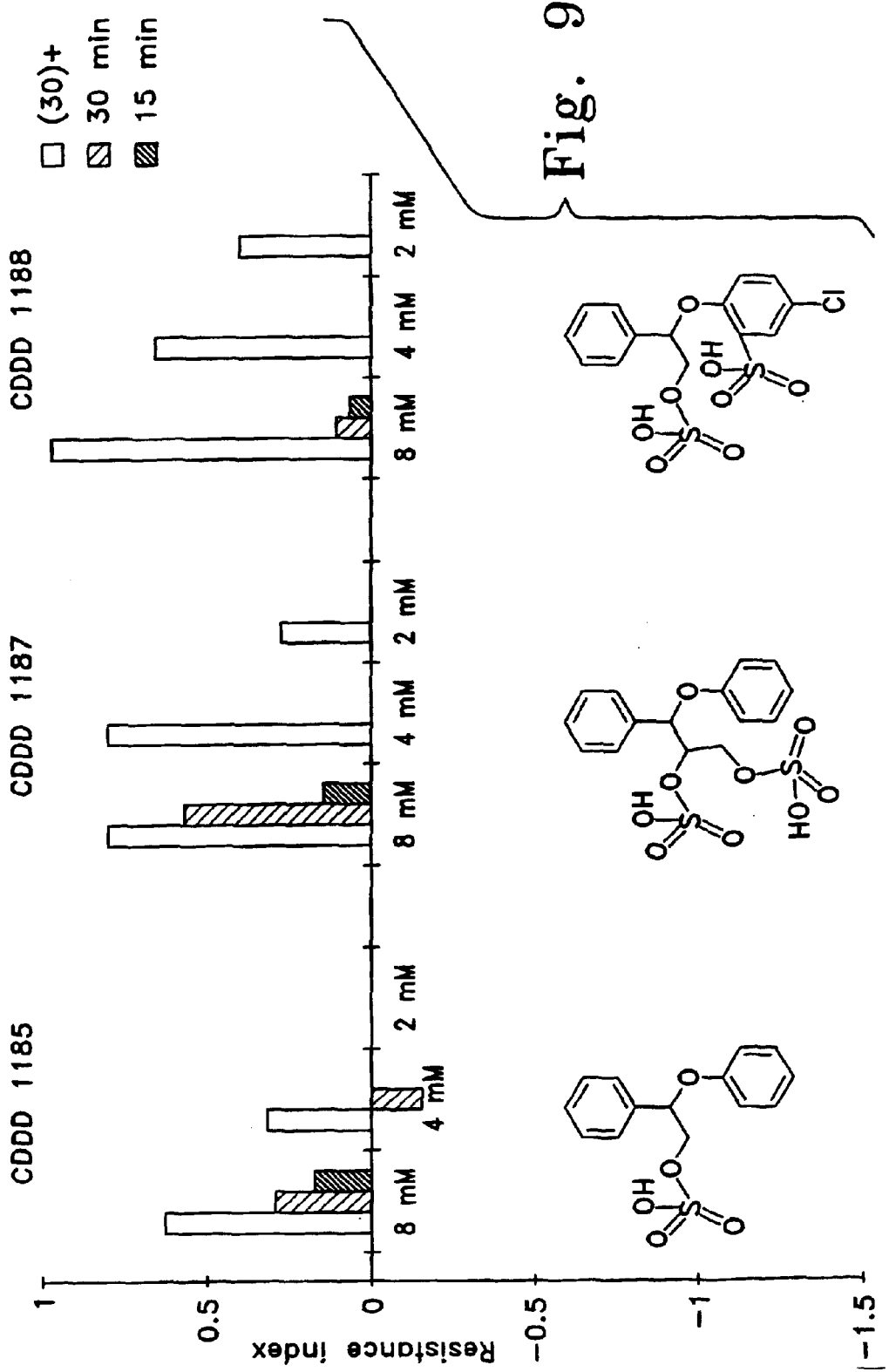
FIG. 9 is a graph showing the protective effects of additional novel sulfate esters of the invention (CDDD-1185, 1187 and 1188) on the esophagus after varying lengths of exposure.

FIG. 9 is a graph showing the protective effects of CDDD-1185, 1187 and 1188 on the esophagus after varying lengths of exposure. Rabbit esophageal epithelium mounted in Ussing chambers is exposed luminally to 2 mM, 4 mM, and/or 8 mM CDDD-1185, 1187, 1188, or to vehicle alone (normal Ringer solution) for 15 min, 30 min, and/or >30 min (approximately 30–60 minutes) prior to the luminal addition of 60 mM HCl, pH 1.6, for 1 hour. Electrical resistance, R, was monitored and the Resistance Index (RI)=$[(R_{agent}/R_{control})-1]$ was plotted at the end of 1 hour of acid exposure. A RI of >0.2 is considered significant. The Figure shows that all three compounds may have significant protective activity at millimolar concentrations. N=1 tissue/dose.

Example 8

Method of Administration of Agent In vivo Prior To Assessing Esophageal Protection Against Acid Injury in Ussing Chamber Method Above.

New Zealand white rabbits weighing between 8–9 lbs were given 25 ml of water containing test agent or water alone (control) to drink once each morning on 4 consecutive days. Following consumption of the 25 ml of water, the rabbits had their normal water source restored and they ate and drank normally for the remainder of each day. Twenty-four hours after the last dose, the rabbits were sacrificed by administering an intravenous overdose of phenobarbital (60 mg/mL). The esophagus was excised and processed as above to test its ability to resist acid injury upon exposure to 60 mM HCl, pH 1.6, for 1 hr. Three sections of rabbit esophageal epithelium that had been exposed to test agent and three sections exposed to water alone (control) were mounted, equilibrated and then simultaneously exposed to acid on the same day without the operator being aware of which were treated and which were control sections of epithelium. Initial R values in all experiments were similar preacidification. Post-acid R values were presented as percent decline from initial (preacidification) R, with protection by the agent being established if there was significantly less of a decline in R upon acid exposure at 1 hr than for the control tissues. Significance was taken as a difference in values of p<0.05.

Figure 10A:
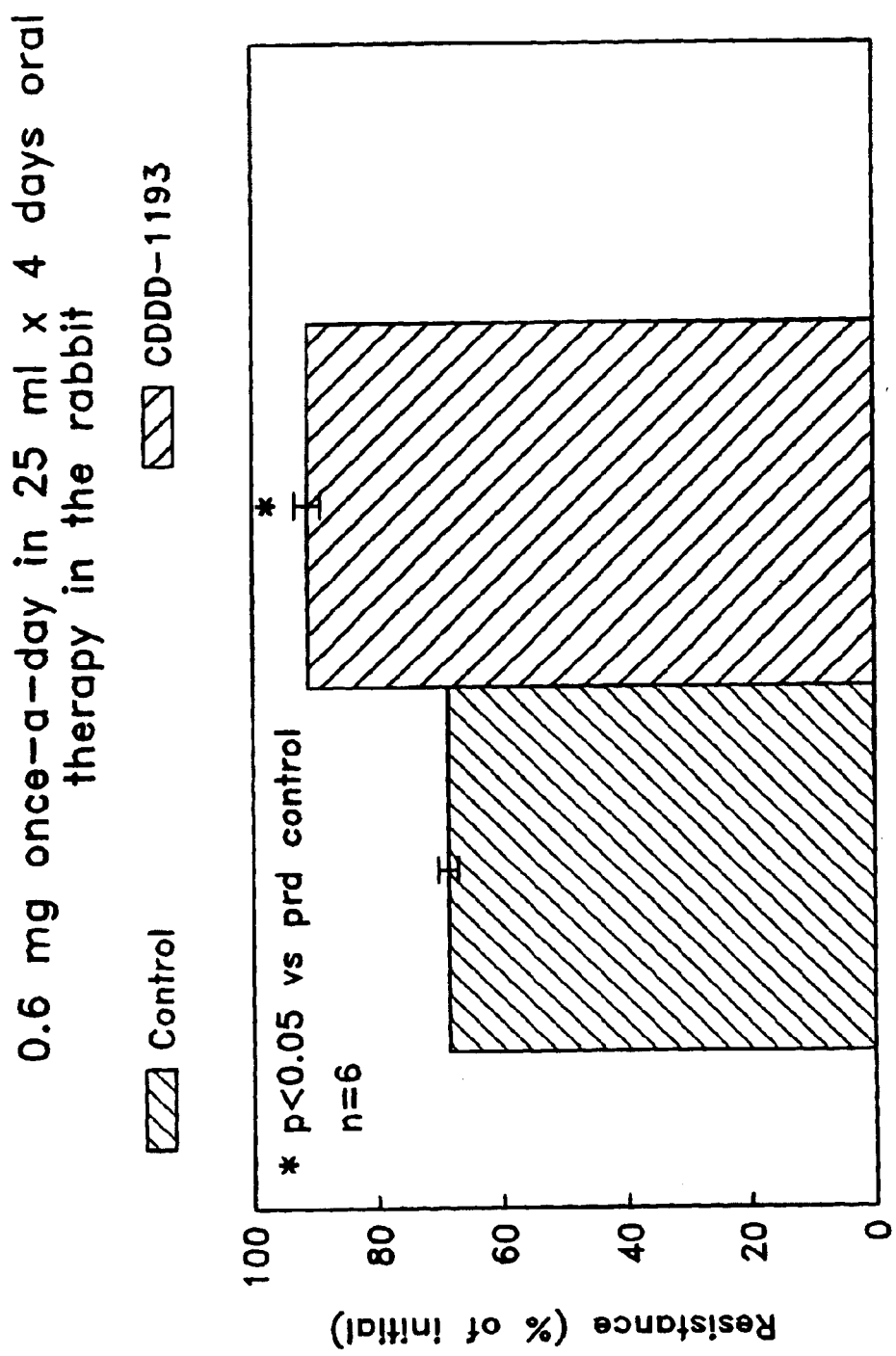
FIGS. 10A and 10B are graphs showing the protective effect after in vivo delivery of CDDD-1193 in drinking water.
Figure 10B:
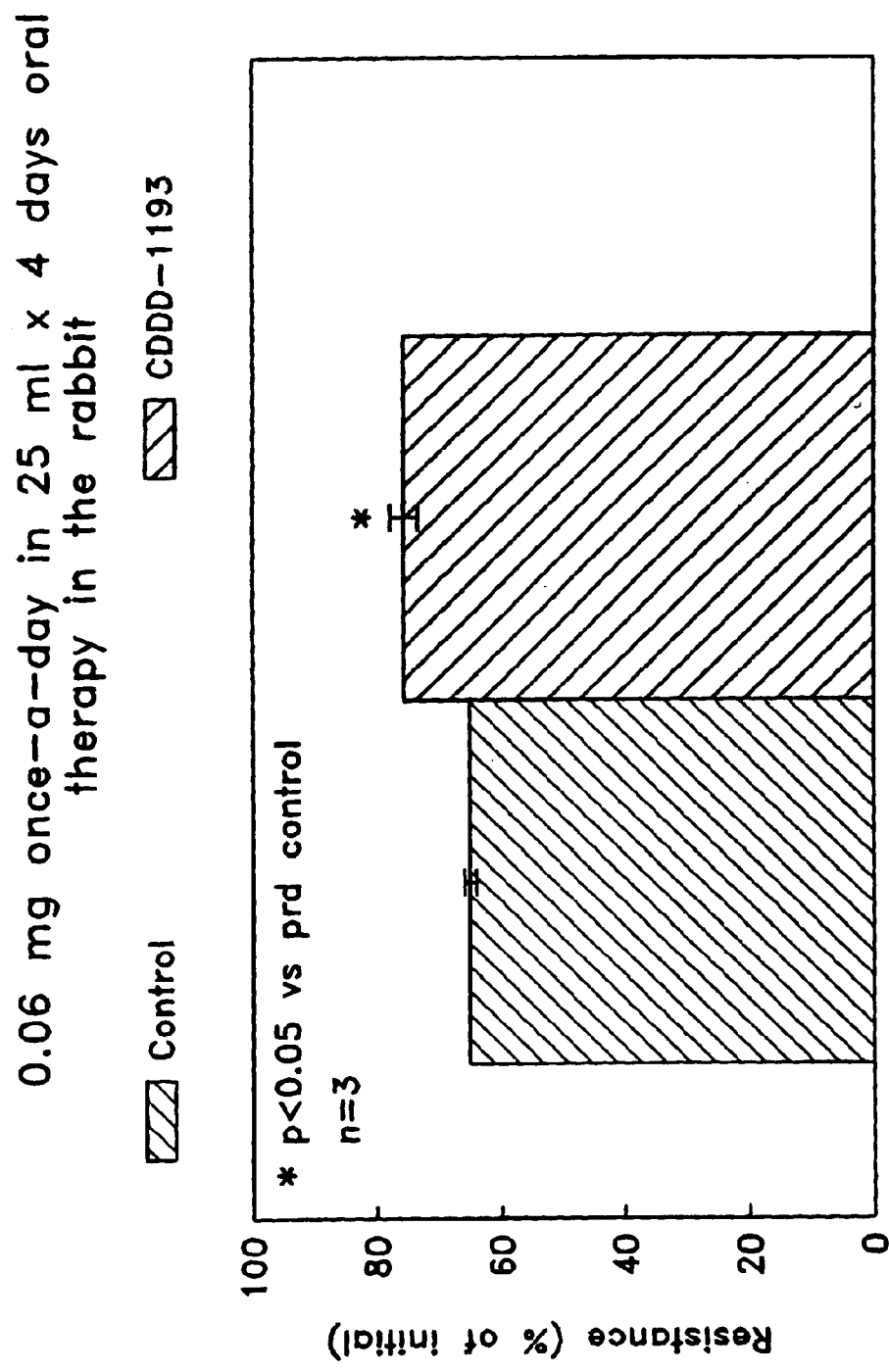

FIGS. 10A and 10B are graphs showing the protective effect after in vivo delivery of CDDD-1193 in drinking water. A rabbit spontaneously drank 25 ml of water containing 0.6 mg or 0.06 mg CDDD-1193 (40 $\mu$M or 4 $\mu$M) once-a-day for 4 consecutive days or water alone. On day 5, the rabbits were sacrificed and three sections of esophageal epithelium mounted in Ussing chambers from each rabbit. After equilibration in Ringer solution, all tissues were acidified by luminal addition of 60 mM HCl, pH 1.6, for 1 hour. Electrical resistance, R, was monitored and plotted as percent initial R (%) at the end of 1 hour of acid exposure. FIG. 10A is a graph showing that 40 $\mu$M CDDD-1193 was significantly protective in this model and that its protective effects last at least for 24 hrs after the last dose. N=6 tissues; *p<0.05 compared to controls. FIG. 10B is a graph showing that 4 $\mu$M CDDD-1193 was also significantly protective in this model and that its protective effects last at least 24 hrs after the last dose. N=3 tissues; *p<0.05 compared to controls.

Figure 11:
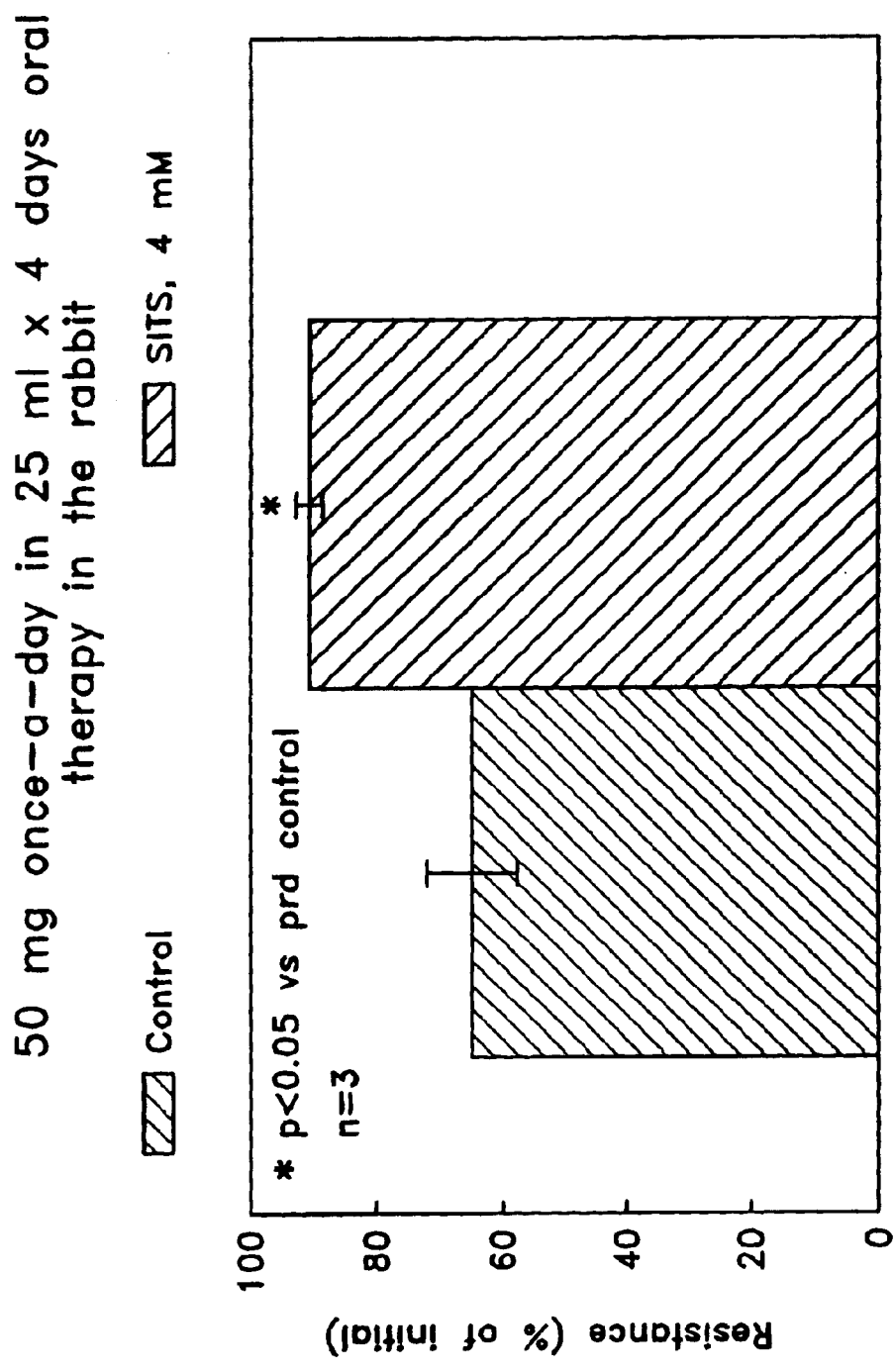
FIG. 11 is a graph showing the protective effect after in vivo delivery of 4 mM SITS in drinking water.

FIG. 11 is a graph showing the protective effect after in vivo delivery of 4 mM SITS in drinking water. A rabbit spontaneously drank 25 ml of water containing 50 mg SITS (4 mM) once-a-day for 4 consecutive days or vehicle alone. On day 5, the rabbits were sacrificed and three sections of esophageal epithelium from each rabbit were mounted in Ussing chambers from each rabbit. After equilibration in Ringer solution, all tissues were acidified by luminal addition of 60 mM HCl, pH 1.6, for 1 hour. Electrical resistance, R, was monitored and plotted as percent initial R (%) at the end of 1 hour of acid exposure. The Figure shows that 4 mM SITS was significantly protective in this model and that its protective effects last for at least 24 hrs after the last dose. N=3 tissues; *p<0.05 compared to controls.

Figure 12:
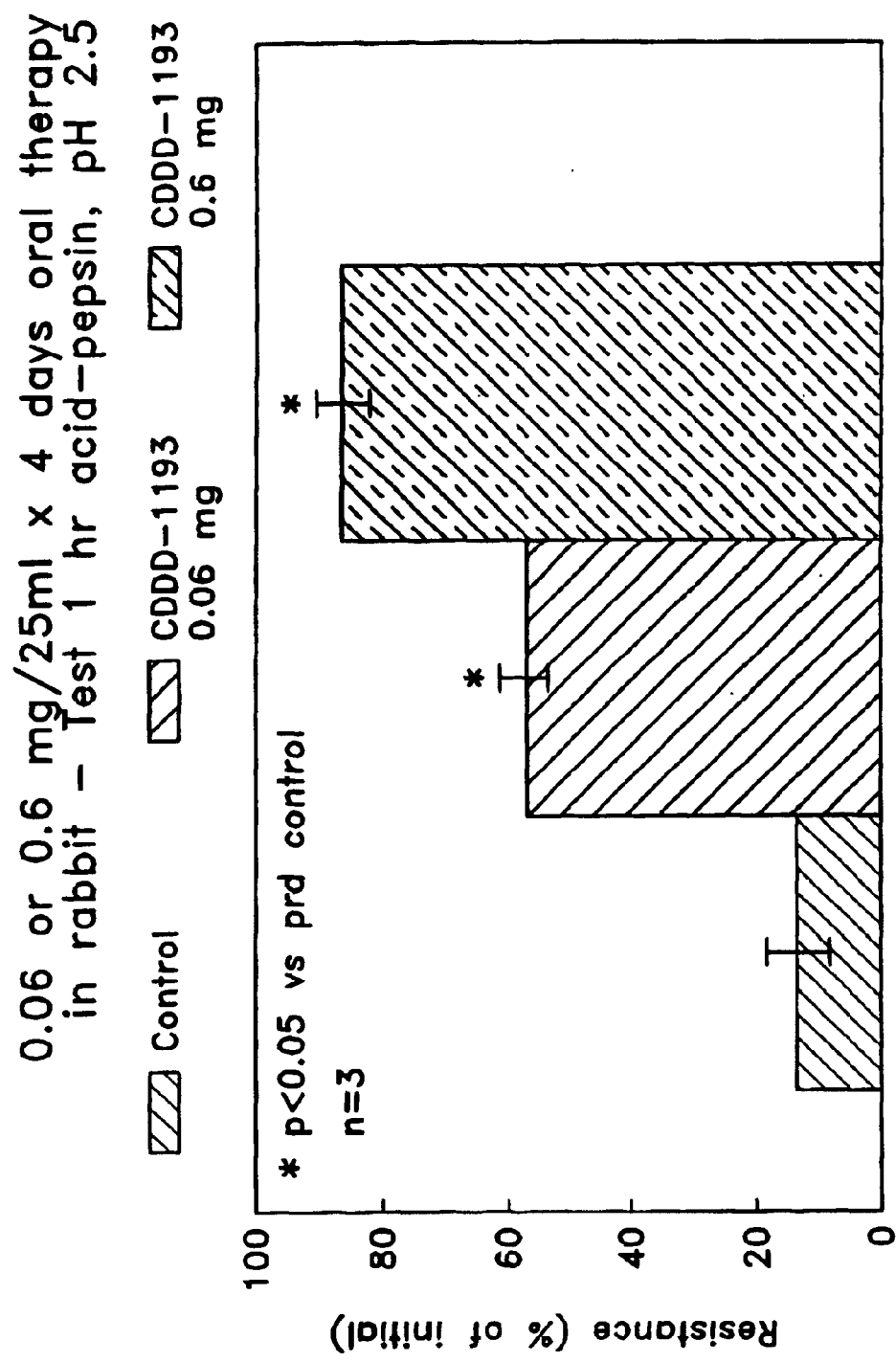
FIG. 12 is a graph showing the protective effect against acid-pepsin after in vivo delivery of CDDD-1193 in drinking water.

FIG. 12 is a graph showing the protective effect against an acid-pepsin mixture after in vivo delivery of CDDD-1193 in drinking water. A rabbit spontaneously drank 25 ml of water containing 0.6 mg (40 $\mu$M) or 0.06 mg (4 $\mu$M) CDDD-1193 once-a-day for 4 consecutive days or water alone. On day 5, the rabbits were sacrificed and three sections of esophageal epithelium mounted in Ussing chambers from each rabbit. After equilibration in Ringer solution, all tissues were acidified by luminal addition of 60 mM HCl, pH 1.6, containing 1 mg/ml pepsin, for 1 hour. Electrical resistance, R, was monitored and plotted as percent initial R (%) at the end of 1 hour of acid-pepsin exposure. The figure shows that 40 $\mu$M and 4 $\mu$M CDDD-1193 were both significantly protective in this model and that this protective effect lasts at least 24 hours after the last dose. N=3 tissues; * p<0.05 compared to controls.

Modifications of the above described modes for carrying out the invention that are obvious to those of ordinary skill in the chemical, pharmaceutical, or related arts are intended to be within the scope of the following claims.

What is claimed is:

1. An agent which protects stratified squamous epithelium against injury by a noxious substance, and has the formula:

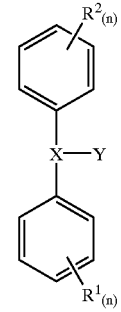

wherein: X is a linker selected from the group consisting of $C_1$–$C_6$ alkylene, $C_2$–$C_6$ alkenylene, or $C_3$–$C_6$ alkynylene, wherein X may optionally include 1 or 2 oxygen atoms and/or 1 sulfur atom;

Y is a group pendant from X, wherein Y is a $C_1$–$C_{10}$ alkyl, $C_2$–$C_{10}$ alkenyl, $C_2$–$C_{10}$ akynyl, or aromatic group to which is attached at least one —$OSO_3R^4$ moiety, and, optionally, at least one OH group, wherein $R^4$ is H or a pharmaceutically acceptable cation;

n is a integer from 1–3; and $R^1$ and $R^2$ are each independently selected from the group consisting of —H, —F, —Cl, —Br, —I, hydroxy, —$SO_3R^4$, —$OSO_3R^4$, —NCS, —NCO, NH(CO)—$OR^3$, —NH(CS)$SR^3$, —NH(C=NH)$OR^3$, —$NHCOCH_2Cl$, —$NHCOCH_2Br$, —NHCO—CH=$CH_2$, —NHC(O)—$CF_3$, —S—$CH_2$—CH=$CH_2$, —$NHCH_2$—C=CH, —NH—$CH_2$—CN, —NH—S—$CH_2$—CH=$CH_2$, —O—$CH_2$—CH=$CH_2$, —NH—$CF_3$, N-mono-, di-, tri-, tetra-, and penta-halochtyl, —CN, —$NH_2$, —$NO_2$, —$NHCOCH_3$, —CHO, —$COOR^4$, —$N_3$, —$COR^3$, —$R^3OH$, —$R^3NHCOCH_3$, —$R^3OSO_3R^4$, —$OR^3$, —$SR^3$, and —$R^3$, wherein —$R^3$ is p-nitrophenyl, $C_1$–$C_6$ alkyl, $C_2$–$C_6$ alkenyl, $C_2$–$C_6$ alkynyl, if at the distal end of the substituent, or $C_1$–$C_6$ alkylene, $C_2$–$C_6$ alkenylene, or $C_2$–$C_6$ alkynylene, if at the proximal end of the substiuent, and wherein $R^4$ is H or a pharmaceutically acceptable cation.

2. The agent of claim 1, wherein at least one of $R^1$ and $R^2$ is —NCS.

3. The agent of claim 1, wherein X is —$OCH_2$—, or —$CH_2O$—.

4. The agent of claim 1, wherein Y is $C_1$ to $C_4$ alkyl, to which is attached at least one —$OSO_3R^4$ moiety.

5. The agent of claim 1, wherein Y is a sulfonated polycarbinol chain of 1 to 6 sulfonated carbon atoms.

6. The agent of claim 1, wherein at least two —OSO$_3$R$^4$ moieties are attached to Y.

7. The agent of claim 1, wherein Y is ethyl-1,2-disulfate.

8. The agent of claim 1, wherein the agent is selected from the group consisting of:

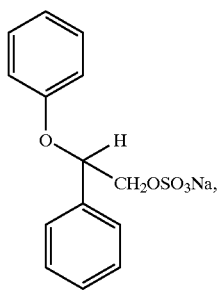

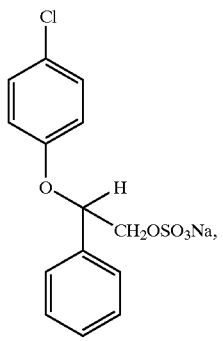

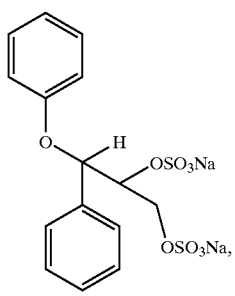

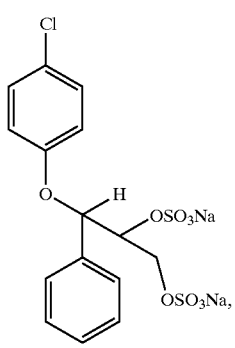

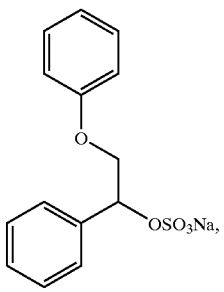

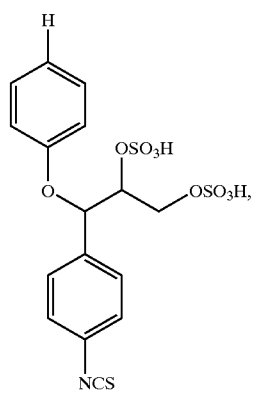

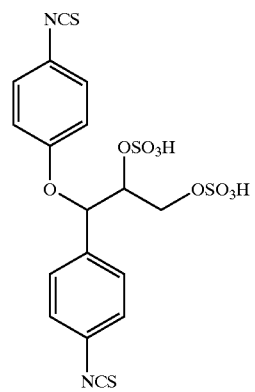

or pharmaceutically acceptable salts thereof.

9. The agent of claim 8, wherein the agent is

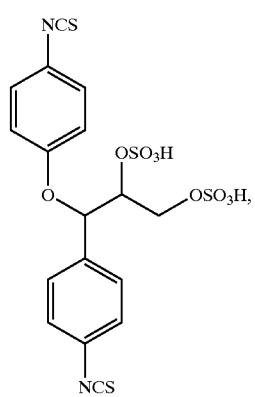

or a pharmaceutically acceptable salt thereof.

10. The agent of claim 8, wherein the agent is

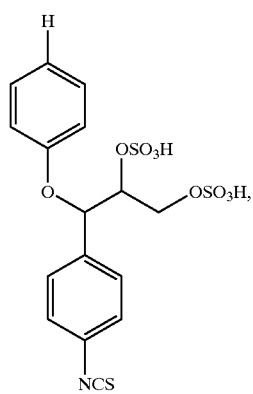

or a pharmaceutically acceptable salt thereof.

11. A composition comprising an agent according to claim 1 and a pharmaceutically acceptable excipient.

12. A composition comprising an agent according to claim 1 and a proton pump inhibitor.

13. The agent of claim 1, wherein from 2 to 6 —$OSO_3R^4$ moieties are attached to Y.

14. The agent of claim 1, wherein Y is $C_1$–$C_6$ alkyl, $C_2$–$C_6$, alkenyl, or $C_3$–$C_6$ alkynyl.

* * * * *